(12) United States Patent
Ishida et al.

(10) Patent No.: US 9,469,621 B2
(45) Date of Patent: Oct. 18, 2016

(54) METHOD FOR PRODUCING MULTISUBSTITUTED BIPHENYL COMPOUND AND SOLID CATALYST TO BE USED THEREIN

(71) Applicants: KYUSHU UNIVERSITY, NATIONAL UNIVERSITY CORPORATION, Fukuoka-shi, Fukuoka (JP); UBE INDUSTRIES, LTD., Ube-shi, Yamaguchi (JP)

(72) Inventors: Tamao Ishida, Fukuoka (JP); Makoto Tokunaga, Fukuoka (JP); Akiyuki Hamasaki, Fukuoka (JP); Syohei Aikawa, Fukuoka (JP); Yoshiyuki Mise, Fukuoka (JP); Tetsuro Tsuji, Ube (JP); Yasushi Yamamoto, Ube (JP); Mitsuru Miyasaka, Ube (JP)

(73) Assignees: KYUSHU UNIVERSITY, NATIONAL UNIVERSITY CORPORATION, Fukuoka (JP); UBE INDUSTRIES, LTD., Ube (JP)

( * ) Notice: Subject to any disclaimer, the term of this patent is extended or adjusted under 35 U.S.C. 154(b) by 0 days.

(21) Appl. No.: 14/434,556

(22) PCT Filed: Oct. 9, 2013

(86) PCT No.: PCT/JP2013/077530
§ 371 (c)(1),
(2) Date: Apr. 9, 2015

(87) PCT Pub. No.: WO2014/057992
PCT Pub. Date: Apr. 17, 2014

(65) Prior Publication Data
US 2015/0274689 A1 Oct. 1, 2015

(30) Foreign Application Priority Data
Oct. 10, 2012 (JP) ................. 2012-225136

(51) Int. Cl.
*B01J 21/06* (2006.01)
*B01J 23/96* (2006.01)
*B01J 38/56* (2006.01)
*B01J 38/52* (2006.01)
*B01J 23/89* (2006.01)
*C07C 67/343* (2006.01)
*B01J 23/68* (2006.01)
(Continued)

(52) U.S. Cl.
CPC ............ *C07D 307/89* (2013.01); *B01J 21/063* (2013.01); *B01J 21/066* (2013.01); *B01J 23/52* (2013.01); *B01J 23/66* (2013.01); *B01J 23/68* (2013.01); *B01J 23/688* (2013.01); *B01J 23/892* (2013.01); *B01J 23/894* (2013.01); *B01J 23/8906* (2013.01); *B01J 23/8913* (2013.01); *B01J 23/96* (2013.01); *B01J 38/52* (2013.01); *B01J 38/56* (2013.01); *C07B 37/04* (2013.01); *C07C 2/84* (2013.01); *C07C 17/269* (2013.01); *C07C 37/11* (2013.01); *C07C 67/343* (2013.01); *C07C 67/465* (2013.01); *B01J 38/50* (2013.01); *C07C 2523/52* (2013.01); *C07C 2523/66* (2013.01); *C07C 2523/68* (2013.01); *C07C 2523/75* (2013.01); *C07C 2523/89* (2013.01); *Y02P 20/52* (2015.11); *Y02P 20/584* (2015.11)

(58) Field of Classification Search
CPC ...... B01J 21/063; B01J 23/96; B01J 21/066; B01J 38/56; B01J 38/52; B01J 23/894; B01J 23/68; B01J 38/50; C07C 67/343; C07C 2523/75; C07C 2523/52; C07B 37/04; Y02P 20/52; Y02P 20/584
See application file for complete search history.

(56) References Cited

U.S. PATENT DOCUMENTS 5,939,569 A * 8/1999 Jones ............... C07D 301/04
549/512
2003/0088120 A1 5/2003 Yamamoto et al.
2006/0247445 A1 11/2006 Nakayama et al.

FOREIGN PATENT DOCUMENTS

CN 102020622 A 4/2011
CN 102389795 A 3/2012
(Continued)

OTHER PUBLICATIONS

JP 4-257542 A 1992; English translation of abstract, p. 5.*
(Continued)

*Primary Examiner* — Samantha Shterengarts
*Assistant Examiner* — Matt Mauro
(74) *Attorney, Agent, or Firm* — Oliff PLC

(57) ABSTRACT

A method for producing a multisubstituted biphenyl compound is represented by the following formula (2), including a step of coupling a substituted benzene compound represented by the following formula (1) in the presence of a solid catalyst with gold immobilized onto a support.

[Chemical Formula 1]

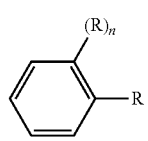

(1)

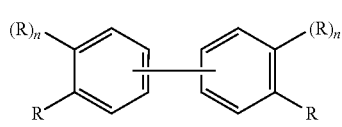

(2)

11 Claims, 3 Drawing Sheets

(51) Int. Cl.
- *C07B 37/04* (2006.01)
- *B01J 38/50* (2006.01)
- *C07D 307/89* (2006.01)
- *B01J 23/66* (2006.01)
- *C07C 2/84* (2006.01)
- *C07C 17/269* (2006.01)
- *B01J 23/52* (2006.01)
- *C07C 37/11* (2006.01)
- *C07C 67/465* (2006.01)

(56) References Cited

FOREIGN PATENT DOCUMENTS

| CN | 102470357 A | 5/2012 |
|---|---|---|
| JP | H04-257542 A | 9/1992 |
| JP | H05-003857 B2 | 1/1993 |
| JP | 3959602 B2 | 8/2007 |
| JP | 4048689 B2 | 2/2008 |
| JP | 2008-259993 A | 10/2008 |
| JP | 2009240951 A * | 10/2009 |
| JP | 4977989 B2 | 7/2012 |
| JP | 2013-209743 A | 10/2013 |
| WO | 2011/010610 A1 | 1/2011 |
| WO | 2012/046857 A1 | 4/2012 |
| WO | 2012/157749 A1 | 11/2012 |

OTHER PUBLICATIONS

JP 2009-240951 ProQuest English machine translation, accessed online Jan. 6, 2016; p. 1-21.*

Takei, T., "Synthesis of acetoaldehyde, acetic acid, and others by the dehydrogenation and oxidation of ethanol." Catalysis Surveys from Asia 15.2 (2011): 80-88.*

Kar et al, "Gold-Catalyzed Direct Oxidative Coupling Reactions of Non-Activated Arenes", Journal of Organometallic Chemistry, 2009, pp. 524-537, vol. 694.

Apr. 14, 2015 Internatioal Preliminary Report on Patentability issued in International Patent Application No. PCT/JP2013/077530.

Nov. 26, 2013 Search Report issued in International Patent Application No. PCT/JP2013/077530.

* cited by examiner

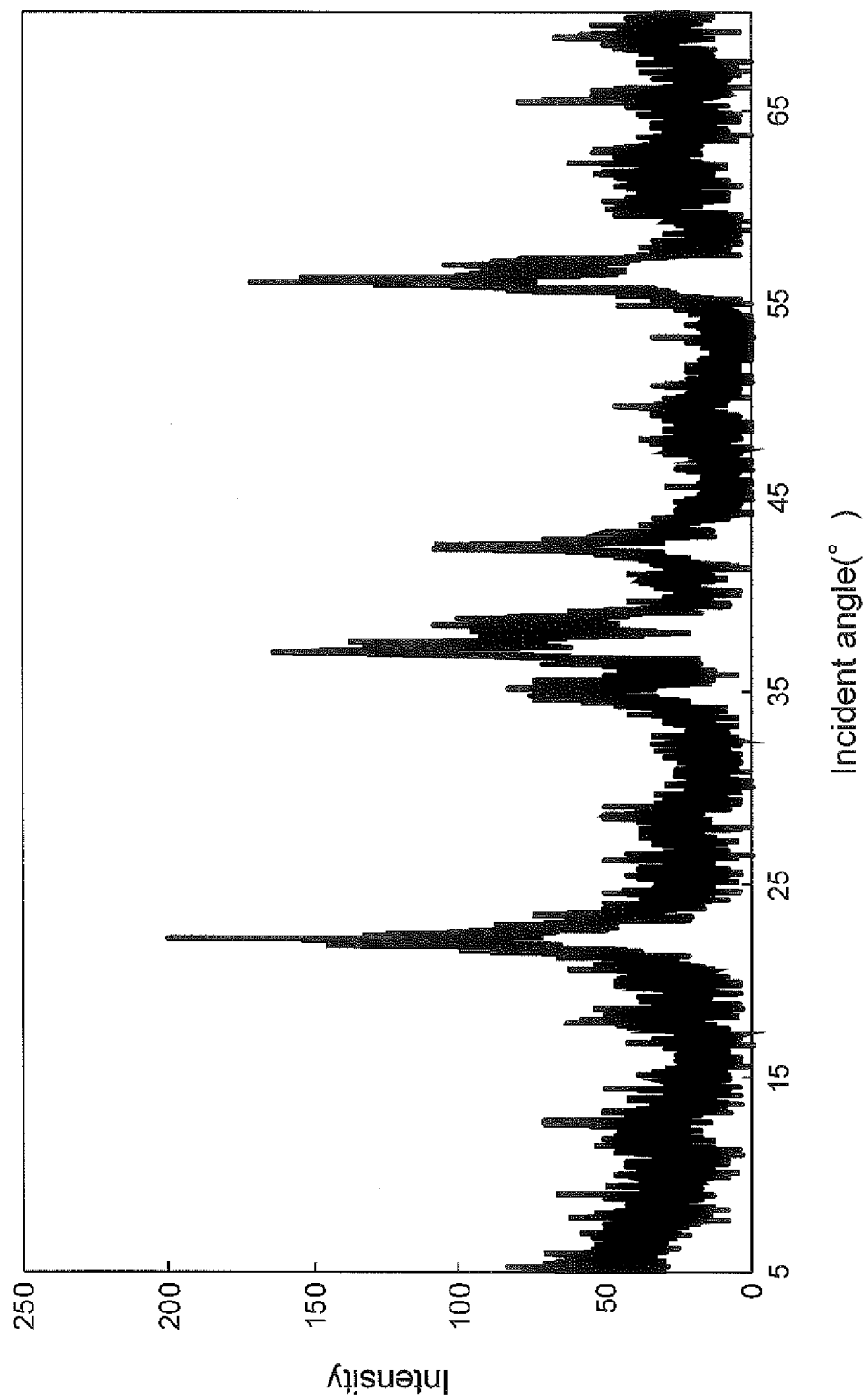

METHOD FOR PRODUCING MULTISUBSTITUTED BIPHENYL COMPOUND AND SOLID CATALYST TO BE USED THEREIN

TECHNICAL FIELD

The present invention relates to a method for producing a multisubstituted biphenyl compound and a solid catalyst to be used therein.

BACKGROUND ART

Conventionally, as a method for producing a multisubstituted biphenyl compound, specifically as a method for producing 3,3',4,4'-biphenyltetracarboxylic acid and an anhydride thereof, for example, is disclosed a method involving dimerizing a halogenated phthalic acid compound in the presence of a palladium catalyst or the like (e.g., see Patent Literature 1).

In addition, as a method for producing 3,3',4,4'-tetramethylbiphenyl, for example, is disclosed a method involving dimerizing o-xylene in the presence of bis(trifluoroacetic acid) palladium, copper acetate and pyridine-2-carboxylic acid (e.g., see Patent Literature 2).

On the other hand, as an example of methods for producing a multisubstituted biphenyl compound using a noble metal catalyst other than palladium, is known a method involving dimerizing a substituted benzene compound using tetrachloroauric acid as a catalyst and particular oxidizing agent, iodobenzene diacetate ($PhI(OAc)_2$) (e.g., see Non Patent Literature 1).

CITATION LIST

Patent Literature

Patent Literature 1: Japanese Examined Patent Publication No. Hei-5-3857
Patent Literature 2: Japanese Patent No. 3959602

Non Patent Literature

Non Patent Literature 1: Journal of Organometallic Chemistry 694 (2009) p. 524-537

SUMMARY OF INVENTION

Technical Problem

Any of the above methods are problematic, since the reaction system is complicated or the catalyst life is short. Additionally, when a homogeneous catalyst is used, problems lie in the fact that it is difficult to recover or reuse the catalyst after the reaction, or a reactor to be used is limited, and accordingly there is required an industrially-suitable method for producing a multisubstituted biphenyl compound.

It is the object of the present invention to provide a method for producing a multisubstituted biphenyl compound and a solid catalyst to be used therein, which enable to obtain a multisubstituted biphenyl compound in a high yield without any complicated steps.

Solution to Problem

The present invention provides a method for producing a multisubstituted biphenyl compound represented by the following formula (2), comprising:

a step of coupling a substituted benzene compound represented by the following formula (1) in the presence of a solid catalyst with gold immobilized onto a support,

[Chemical Formula 1]

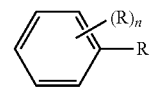

(1)

wherein R represents an alkyl group, an alkoxy group, a hydroxy group, or a carboxyl group which may be esterified, and n represents an integer of 0 to 3; when n is any integer of 1 to 3, a plurality of R may be the same or different from each other; and when n is any integer of 1 to 3 and both of two R bonding to adjacent carbon atoms are the carboxyl groups, these carboxyl groups may bond to each other to form an anhydride,

[Chemical Formula 2]

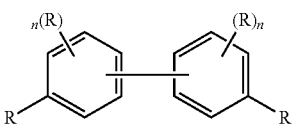

(2)

wherein R represents an alkyl group, an alkoxy group, a hydroxy group, or a carboxyl group which may be esterified, and n represents an integer of 0 to 3; a plurality of n and R may be the same or different from each other; and when n is any integer of 1 to 3 and both of two R bonding to adjacent carbon atoms are the carboxyl groups, these carboxyl groups may bond to each other to form an anhydride.

According to the above production method, a multisubstituted biphenyl compound can be obtained in a high yield without any complicated steps.

It is preferable that the substituted benzene compound represented by the above formula (1) be a substituted benzene compound represented by the following formula (1)' and the multisubstituted biphenyl compound represented by the above formula (2) be a compound represented by the following formula (2)',

[Chemical Formula 3]

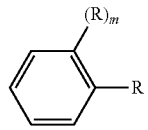

(1)' wherein R represents an alkyl group, an alkoxy group, a hydroxy group, or a carboxyl group which may be esterified, and m represents 0 or 1; when m is 1, two R may be the same or different from each other; and when m is 1 and both of two R are the carboxyl groups, these carboxyl groups may bond to each other to form an anhydride,

[Chemical Formula 4]

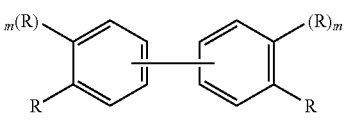

(2)' wherein R represents an alkyl group, an alkoxy group, a hydroxy group, or a carboxyl group which may be esterified, and m represents 0 or 1; a plurality of m and R may be the same or different from each other; and when m is 1 and both of two R bonding to adjacent carbon atoms are the carboxyl groups, these carboxyl groups may bond to each other to form an anhydride.

The R in the above formulae (1) and (2) or the above formulae (1)' and (2)' is preferably an alkyl group, a carboxyl group or an alkoxycarbonyl group, more preferably an alkyl group or an alkoxycarbonyl group.

It is preferable that m be 1 in the above formulae (1)' and (2)' and the production ratio (s/a ratio) be 2.0 or more. The s/a ratio is the production ratio of the s-form represented by the following formula (2s) to a-form represented by the following formula (2a) in the multisubstituted biphenyl compound represented by the above formula (2)',

[Chemical Formula 5]

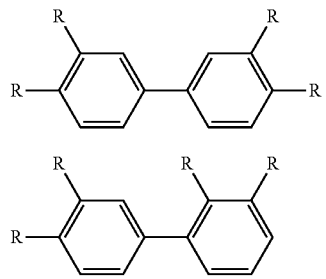

(2s)

(2a)

wherein R represents an alkyl group, an alkoxy group, a hydroxy group, or a carboxyl group which may be esterified; a plurality of R may be the same or different from each other; and when both of two R bonding to adjacent carbon atoms are the carboxyl groups, these carboxyl groups may bond to each other to form an anhydride.

In the above step, it is preferable to couple the substituted benzene compound represented by the above formula (1) further in the presence of a solvent, and the solvent is more preferably an organic carboxylic acid, and the organic carboxylic acid is further preferably acetic acid. A multisubstituted biphenyl compound can be obtained in an even higher yield by using the solvent. In addition, when a compound in which m is 1 in the above formula (1)' is used as a substrate, a multisubstituted biphenyl compound can be obtained in a high s/a ratio.

In the above step, it is preferable to couple the substituted benzene compound represented by the above formula (1) in a gas containing oxygen. A multisubstituted biphenyl compound can be obtained in an even higher yield by performing the coupling reaction in a gas containing oxygen.

The present invention also provides a solid catalyst for producing a multisubstituted biphenyl compound represented by the following formula (2), the solid catalyst comprising a support and gold immobilized onto the support,

[Chemical Formula 6]

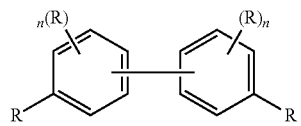

(2)

wherein R represents an alkyl group, an alkoxy group, a hydroxy group, or a carboxyl group which may be esterified, and n represents an integer of 0 to 3; a plurality of n and R may be the same or different from each other; and when n is any integer of 1 to 3 and both of two R bonding to adjacent carbon atoms are the carboxyl groups, these carboxyl groups may bond to each other to form an anhydride.

A multisubstituted biphenyl compound can be obtained in a high yield without any complicated steps by using the solid catalyst.

The present invention also provides a use of a solid catalyst comprising a support and gold immobilized onto the support, for producing a multisubstituted biphenyl compound represented by the following formula (2),

[Chemical Formula 7]

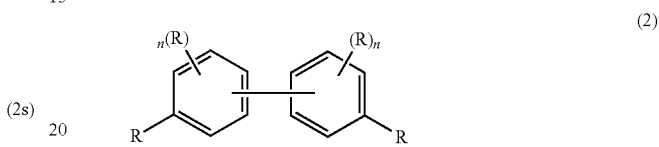

(2)

wherein R represents an alkyl group, an alkoxy group, a hydroxy group, or a carboxyl group which may be esterified, and n represents an integer of 0 to 3; a plurality of n and R may be the same or different from each other; and when n is any integer of 1 to 3 and both of two R bonding to adjacent carbon atoms are the carboxyl groups, these carboxyl groups may bond to each other to form an anhydride.

It is preferable that the support be a metal oxide. There is a tendency that the catalyst life is prolonged or the reaction rate is accelerated when the support is a metal oxide.

Moreover, the metal oxide is preferably an oxide of at least one metal selected from the group consisting of cobalt (Co), manganese (Mn), iron (Fe), cerium (Ce), zirconium (Zr), nickel (Ni), titanium (Ti), lanthanum (La), silicon (Si) and aluminum (Al), and more preferably an oxide of at least one metal selected from the group consisting of manganese (Mn), cobalt (Co) and zirconium (Zr). A multisubstituted biphenyl compound can be obtained in an even higher yield by using the metal oxide.

It is preferable that a gold particle having an average particle diameter of 0.5 to 10 nm be immobilized onto the support. When the average particle diameter of the gold particle is within the range, the yield and reaction rate of the coupling reaction is highly improved. When a compound in which m is 1 in the above formula (1)' is used as a substrate, a multisubstituted biphenyl compound can be obtained in a high s/a ratio.

Advantageous Effects of Invention

According to the present invention, there can be provided a method for producing a multisubstituted biphenyl compound and a solid catalyst to be used therein, which enable to obtain the multisubstituted biphenyl compound in a high yield without any complicated steps. In addition, the solid catalyst obtained according to the present invention can be recovered and reused after the reaction.

BRIEF DESCRIPTION OF DRAWINGS

FIG. 3 is an X-ray diffraction pattern of manganese dioxide obtained in Reference Example 1-21.

DESCRIPTION OF EMBODIMENTS

Figure 1:
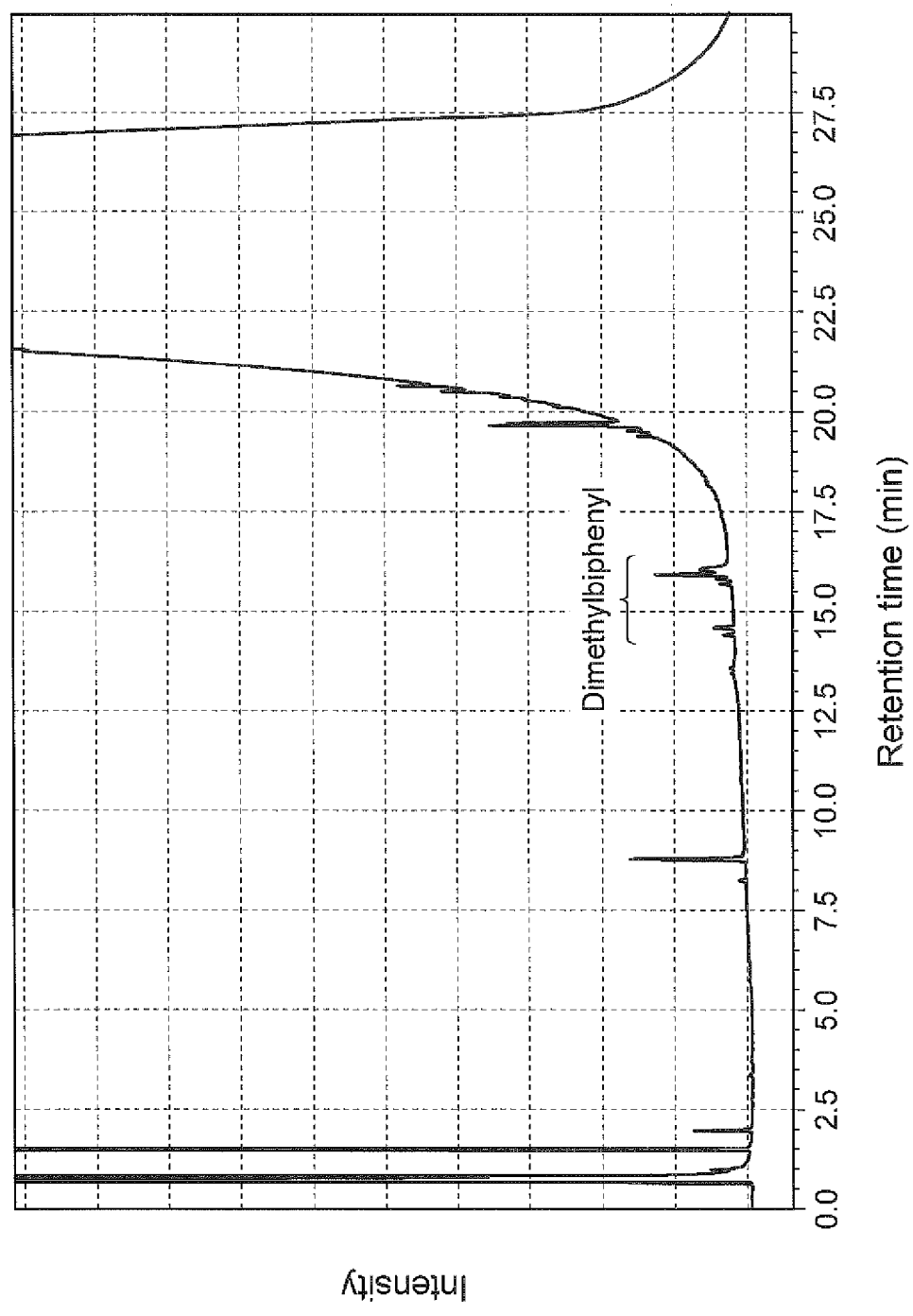
FIG. 1 is a chart of gas chromatography for a reaction solution obtained in Example 2-38.

Hereinafter, a preferred embodiment of the present invention will be described in detail. However, the present invention is never limited to the following embodiment.

The method for producing a multisubstituted biphenyl compound in the present embodiment comprises a step of coupling a substituted benzene compound to the same type of compound in the presence of a solid catalyst.

(Solid Catalyst)

The solid catalyst in the present embodiment is one in which gold is physically or chemically immobilized (sometimes referred to "supported") onto a support. It is to be noted that a primary particle diameter of a solid catalyst described below means a diameter of each particle (primary particle) constituting the solid catalyst. Further, a particle diameter of a gold particle means a particle diameter of each gold particle immobilized onto the solid catalyst.

The shape of a solid catalyst may be selected appropriately depending on an aspect in which the solid catalyst is used, and is preferably particulate. Moreover, the form of a solid catalyst may be any form such as a dense body and a porous body. The average primary particle diameter of a solid catalyst is preferably 5 nm to 1 mm, more preferably 5 nm to 10 μm and further preferably 5 nm to 100 nm. The average primary particle diameter described here is a number-based average value of diameters calculated by determining a particle diameter distribution using scanning electron microscope (SEM) observation, transmission electron microscope (TEM) observation or laser diffraction scattering type particle diameter distribution measuring apparatus.

In the solid catalyst, it is preferable that the gold be immobilized onto the support in a film or particulate state and more preferably immobilized in a particulate state.

When the gold is immobilized onto the support in a particulate state, it is desirable that the particle diameters of immobilized gold particles be uniform. The average particle diameter of the gold particles is preferably 20 nm or less, more preferably 10 nm or less, further preferably 5 nm or less, and preferably 0.5 nm or more. When the average particle diameter of the gold particles is within the range, the efficiency of the coupling reaction per unit mass of the immobilized gold, i.e., the turnover number per unit time can be enhanced.

In the present embodiment, it is desirable that gold be immobilized onto the surface of the support in a homogenously dispersed manner. The dispersion state is controlled by the amount of gold to be immobilized onto a support, a support to be selected, a method for immobilizing gold onto a support, and the like.

The amount of gold to be immobilized onto a support may be depend on the state and size (particle diameter in the case of a particle) of the gold. The amount of gold to be immobilized onto a support is preferably 0.01 to 30% by mass, more preferably 0.1 to 15% by mass based on the whole solid catalyst. There is a tendency that a desirable reaction rate can be obtained even with a small amount of a solid catalyst when the amount of immobilized gold is equal to or more than the lower limit value of the range, and the efficiency of the coupling reaction per unit mass of immobilized gold, i.e., the turnover number per unit time can be enhanced to provide economic advantage when the amount of gold to be immobilized is equal to or less than the upper limit value of the range.

The average particle diameter of gold particles immobilized onto a support can be evaluated by determining a particle diameter distribution of the gold particles using transmission electron microscope (TEM) observation. The amount of metal in a solid catalyst (e.g., the amount of immobilized gold) can be measured by using, for example, inductively coupled plasma-atomic emission spectroscopy (ICP-AES). Further, an atomic species present in a solid catalyst or the dispersion state of gold can be confirmed with a transmission electron microscope (TEM), electron spectroscopy for chemical analysis (ESCA), X-ray diffraction (XRD) or the like.

The support is not particularly limited as long as it is generally used as a support for a solid catalyst, and both inorganic and organic compounds can be employed. Examples of the support include metal oxides such as nickel oxide, zinc oxide, iron oxide, cobalt oxide, manganese dioxide, copper oxide, silicon oxide, tin oxide, aluminum oxide, barium oxide, titanium oxide, vanadium oxide, tungsten oxide, molybdenum oxide, niobium oxide, tantalum oxide, cerium oxide, yttrium oxide, zirconium oxide, lanthanum oxide, magnesium oxide, beryllium oxide, chromium oxide, scandium oxide, cadmium oxide and indium oxide, or complex oxides in which these metal oxides are combined; activated carbon; carbon black; organic polymers; zeolites; mesoporous silicates; clay; diatomaceous earth; and pumice. The support is preferably composed of an inorganic compound because, for example, it can be easily produced and it can be used at a high temperature, and more preferably the support is composed of a metal oxide. There is a tendency that the catalyst life is prolonged or the reaction rate is accelerated when the support is a metal oxide. Note that these supports may be used singly or two or more thereof may be used in a mixture.

The metal oxide is preferably an oxide of at least one metal selected from the group consisting of cobalt (Co), manganese (Mn), iron (Fe), cerium (Ce), zirconium (Zr), nickel (Ni), titanium (Ti), lanthanum (La), silicon (Si) and aluminum (Al), and more preferably an oxide of at least one metal selected from the group consisting of manganese (Mn), cobalt (Co) and zirconium (Zr). There is a tendency that a multisubstituted biphenyl compound can be obtained in an even higher yield when the above metal oxide is used as a support. In addition, when the above metal oxide is used as a support and a compound in which m is 1 in the above formula (1)' is used as a substrate, a multisubstituted biphenyl compound can be obtained in a high s/a ratio.

The shape of a support used for producing a solid catalyst may be selected appropriately depending on an aspect in which the support is used, and is preferably particulate. Moreover, the form of a support may be any form such as a dense body and a porous body. The size of a support (the average primary particle diameter in the case of a particle) is preferably 5 nm to 1 mm, more preferably 5 nm to 10 μm, and further preferably 5 nm to 100 nm. The size of a support can be measured as a number-based average value of diameters by using, for example, scanning electron microscope (SEM) observation, transmission electron microscope (TEM) observation or laser diffraction scattering type particle diameter distribution measuring apparatus.

The method for producing a solid catalyst is not particularly limited and examples thereof include a coprecipitation method, a deposition-precipitation method, an impregnation method, an evaporation-to-dryness method, a pore-filling method and an ion-exchange method. Among them, a coprecipitation method or a deposition-precipitation method, which are described in the following, are preferable, because gold can be immobilized onto many kinds of supports and the particle diameter of gold immobilized onto a support can be controlled to be small. In a solid catalyst produced by using a coprecipitation method or a deposition-precipitation method, gold tends to be immobilized onto the surface of a support in a homogenously dispersed manner. A solid catalyst with gold immobilized may be calcined under an air atmosphere, a hydrogen atmosphere or an inert gas atmosphere.

[Coprecipitation Method]

An aqueous solution containing a gold compound and a nitrate of a metal concerned which is a precursor of a metal oxide as a support is added to an aqueous solution of a basic compound to be neutralized, and thereby a hydroxide of gold is precipitated along with a carbonate or hydroxide of the metal concerned. The precipitate is washed with water, dried, and thereafter calcined under any atmosphere, and thereby a solid catalyst with gold immobilized can be obtained.

[Deposition-Precipitation Method]

In an aqueous solution of a gold compound whose pH is adjusted in a range of 7 to 10 by adding a basic compound, are suspended or immersed a powder of an oxide as a support, or a compact in which the powder is supported onto a spherical, cylindrical, honeycomb support medium or the like, and thereby a hydroxide of gold is deposited-precipitated on the surface of the oxide support. The support on which the hydroxide of gold has been deposited-precipitated is washed with water, dried, and calcined under any atmosphere, and thereby a solid catalyst with gold immobilized can be obtained. The basic compound described above is appropriately selected depending on a solid catalyst to be prepared, and for example, sodium hydroxide, urea and the like are used.

(Substituted Benzene Compound)

The substituted benzene compound used as a substrate in the coupling reaction of the present embodiment is a compound represented by the following formula (1),

[Chemical Formula 8]

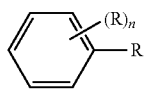

(1)

wherein R represents an alkyl group, an alkoxy group, a hydroxy group, or a carboxyl group which may be esterified, and n represents an integer of 0 to 3; when n is any integer of 1 to 3, a plurality of R may be the same or different from each other; and when n is any integer of 1 to 3 and both of two R bonding to adjacent carbon atoms are the carboxyl groups, these carboxyl groups may bond to each other to form an anhydride.

Furthermore, it is preferable that the substituted benzene compound be a compound represented by the following formula (1)',

[Chemical Formula 9]

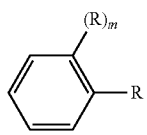

(1)' wherein R represents an alkyl group, an alkoxy group, a hydroxy group, or a carboxyl group which may be esterified, and m represents 0 or 1; when m is 1, two R may be the same or different from each other; and when m is 1 and both of two R are the carboxyl groups, these carboxyl groups may bond to each other to form an anhydride.

The alkyl group of R in the above formulae (1) and (1)' is preferably an alkyl group having 1 to 4 carbon atoms, and each hydrogen atom of the alkyl group may be substituted by a halogen atom. Examples of the alkyl group described above include a methyl group, an ethyl group, a n-propyl group, an isopropyl group, a n-butyl group, an isobutyl group, a trifluoromethyl group and the like, and the alkyl group is preferably a methyl group or an ethyl group.

The alkoxy group of R in the above formulae (1) and (1)' is preferably an alkoxy group having 1 to 5 carbon atoms, and examples thereof include a methoxy group, an ethoxy group, a propoxy group, a butoxy group, a pentyloxy group and the like, and the alkoxy group is preferably a methoxy group and an ethoxy group.

It is preferable that the carboxyl group which may be esterified of R in the above formulae (1) and (1)' be a carboxyl group or an alkyl ester of a carboxyl group (an alkoxycarbonyl group). In the case that a carboxyl group forms an alkyl ester, the alkyl group is preferably an alkyl group having 1 to 6 carbon atoms, and examples thereof include a methyl group, an ethyl group, a propyl group, a butyl group and the like, and the alkyl group is preferably a methyl group or an ethyl group.

Specific examples of the substituted benzene compound represented by the above formula (1)' include toluene, ethylbenzene, butylbenzene, o-xylene, o-dimethoxybenzene, methyl benzoate, butyl benzoate, dimethyl phthalate, diethyl phthalate, phthalic anhydride and the like. Further, specific examples of the substituted benzene compound represented by the above formula (1) other than those represented by the above formula (1)' include trifluoromethylbenzene, p-dimethoxybenzene, 2,3,6-trimethylphenol and the like.

(Solvent)

In the method for producing a multisubstituted biphenyl compound according to the present embodiment, a substituted benzene compound may be coupled to the same type of compound in the presence of a solvent.

When a solvent is used for the coupling reaction, the solvent is not particularly limited as long as it does not inhibit the coupling reaction, and examples thereof include water; organic carboxylic acids such as acetic acid, propionic acid, butanoic acid, pentanoic acid, hexanoic acid and octanoic acid; organic solvents in which any hydrogen on the carbon chain is fluorinated (fluorous solvents) such as 1H,1H-tridecafluoro-1-heptanol, 2H,3H-decafluoropentane, hexafluorobenzene and pentafluorotoluene; ethers such as diethyl ether, tetrahydrofuran and dioxane; organic ester compounds such as ethyl acetate, propyl acetate, butyl acetate, octyl acetate, ethyl propionate, propyl propionate, butyl propionate, octyl propionate, ethylene glycol diacetate and dimethyl adipate; and ketone compounds such as n-butyl methyl ketone, methyl ethyl ketone and isopropyl ethyl ketone. Among them, organic carboxylic acids are preferably used, and more preferably acetic acid is used. Note that one of these solvents may be used singly or two or more thereof may be used in a mixture.

There is a tendency that the reaction rate of the coupling reaction and the regioselectivity of a multisubstituted biphenyl compound can be enhanced when a solvent, preferably an organic carboxylic acid, more preferably acetic acid is used for the coupling reaction. In particular, a multisubstituted biphenyl compound can be obtained in a high s/a ratio when a compound in which m is 1 in the above formula (1)' is used as a substrate.

Furthermore, in the method for producing a multisubstituted biphenyl compound according to the present embodiment, a substituted benzene compound may be coupled to the same type of compound without any solvent, for example, in the presence of only a solid catalyst.

(Coupling Reaction)

The coupling reaction of a substituted benzene compound according to the present embodiment is performed, for example, with a method in which the above solid catalyst and the above substituted benzene compound are reacted while stirring and as necessary mixing with a solvent. The temperature of the coupling reaction is preferably 50 to 250° C., and more preferably 100 to 200° C., and the reaction pressure is preferably 0.1 to 5 MPa, and more preferably 0.1 to 2.5 MPa. Note that the mode of reaction may be any of batch or flow type, gas phase or liquid phase, fixed bed or fluidized bed modes.

The reaction atmosphere for the coupling reaction according to the present embodiment is not particularly limited, and examples thereof include inert gases such as nitrogen, helium and argon; oxidizing gases such as oxygen and ozone. It is preferable that the coupling reaction be performed in an oxidizing gas, and more preferably in a gas containing oxygen. When the coupling reaction is performed in an inert gas, it is preferable that the inert gas be nitrogen. Among them, nitrogen, oxygen, a mixture of nitrogen and oxygen (e.g., air) and the like may be used. Note that another gas which is not involved in the reaction such as carbon dioxide may be contained.

The amount of a solid catalyst to be used for the coupling reaction is determined on the basis of the ratio of the total molar number of a substituted benzene compound to the total molar number of gold immobilized onto a support. It is preferable that the amount of the gold immobilized onto the support be 0.01 mol % to 100 mol %, more preferably 0.03 mol % to 80 mol %, further preferably 0.05 mol % to 50 mol %, and particularly preferably 0.1 mol % to 10 mol % relative to the total molar number of the substituted benzene compound. Hereinafter, the ratio of the molar number of gold immobilized onto a support to the total molar number of a substituted benzene compound is simply represented by the equivalent number (mol %) of a solid catalyst, and sometimes is stated "0.1 mol % relative to a substituted benzene compound" or the like.

When a solvent is used for the coupling reaction, the amount thereof to be used is preferably 0 to 10 mL, and more preferably 0 to 2.5 mL relative to 1 g of a substituted benzene compound.

A multisubstituted biphenyl compound obtained by using the coupling reaction according to the present embodiment can be isolated/purified after the coupling reaction with a common method such as filtration, extraction, distillation, sublimation, recrystallization and column chromatography.

(Multisubstituted Biphenyl Compound)

The multisubstituted biphenyl compound obtained by using the production method according to the present embodiment has the structure represented by the following formula (2),

[Chemical Formula 10]

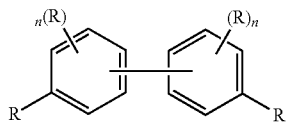

(2)

wherein R represents an alkyl group, an alkoxy group, a hydroxy group, or a carboxyl group which may be esterified, and n represents an integer of 0 to 3; when n is any integer of 1 to 3, a plurality of R may be the same or different from each other; when n is any integer of 1 to 3 and both of two R bonding to adjacent carbon atoms are the carboxyl groups, these carboxyl groups may bond to each other to form an anhydride.

Furthermore, it is preferable that the multisubstituted biphenyl compound be the compound represented by the following formula (2)' obtained by coupling the substituted benzene compound represented by the formula (1)' to the same type of compound,

[Chemical Formula 11]

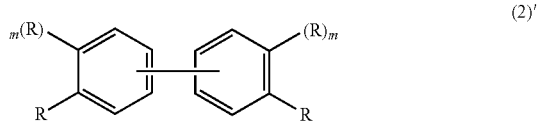

(2)' wherein R represents an alkyl group, an alkoxy group, a hydroxy group, or a carboxyl group which may be esterified, and m represents 0 or 1; a plurality of m or R may be the same or different from each other; when m is 1 and both of two R bonding to adjacent carbon atoms are the carboxyl groups, these carboxyl groups may bond to each other to form an anhydride.

The alkyl group, alkoxy group, and carboxyl group which may be esterified as R in the above formulae (2) and (2)' have the same meanings as those in formulae (1) and (1)'.

The multisubstituted biphenyl compound to be obtained is a disubstituted biphenyl compound when the substituted benzene compound is a compound in which n is 0 in the above formula (1); a tetrasubstituted biphenyl compound in the case of a compound in which n is 1; and a octasubstituted biphenyl compound in the case of a compound in which n is 3. When a substituted benzene compound is coupled by using the production method according to the present embodiment, isomers consisting of a symmetrically-substituted biphenyl (which means a biphenyl having substituents at symmetrical positions on two benzene rings) and an asymmetrically-substituted biphenyl (which means a biphenyl having substituents at asymmetrical positions on two benzene rings) can be obtained. For example, when the substituted benzene compound is the compound in which m is 1 in the above formula (1)', tetrasubstituted biphenyl compounds of a symmetrically-substituted biphenyl represented by the following formula (2s) (hereinafter, sometimes denoted "s-form") and an asymmetrically-substituted biphenyl represented by the following formula (2a) (hereinafter, sometimes denoted "a-form") are generated as the major isomers,

[Chemical Formula 12]

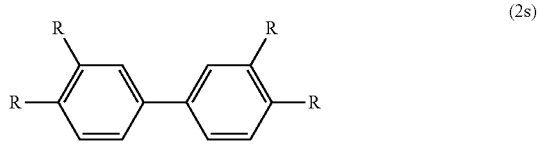

(2s)

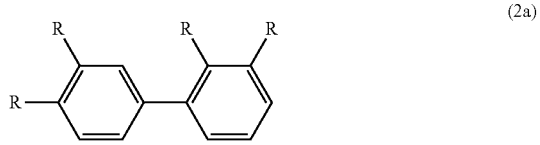

(2a)

wherein, R has the same meaning as that in formula (2).

Here, when R is the above carboxyl group, these carboxyl groups may bond to each other to form an anhydride represented by the following formula (3).

[Chemical Formula 13]

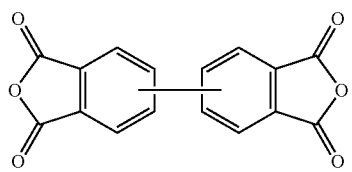

(3)

It is preferable that the yield of the multisubstituted biphenyl compound obtained as described above be, for example, 1% or more, more preferably 3% or more, further preferably 5% or more, and particularly preferably 10% or more. Further, it is preferable that the s/a ratio, which is described in the following, be, for example, 2.0 or more, more preferably 3.0 or more, further preferably 5.0 or more, still further preferably 10.0 or more, and particularly preferably 20.0 or more.

When both of two R bonding to adjacent carbon atoms in the compound represented by the above formula (2) are carboxyl groups and these carboxyl groups bond to each other to form an anhydride, a multisubstituted biphenyl compound forming an anhydride may be synthesized using a method different from the above coupling reaction after synthesizing a multisubstituted biphenyl compound not forming an anhydride using the above coupling reaction.

When R in the compound represented by formula (1) is an alkyl group, the method for producing a multisubstituted biphenyl compound according to the present embodiment may further comprise a step of oxidizing the alkyl group. The oxidizing step allows to convert the R to a carboxyl group. Further, when R in the compound represented by formula (1) is an esterified carboxyl group, the method for producing a multisubstituted biphenyl compound according to the present embodiment may further comprise a step of hydrolyzing the esterified carboxyl group. The hydrolyzing step allows to convert the R to a carboxyl group. Furthermore, when both of two R bonding to adjacent carbon atoms in the compound represented by formula (1) are carboxyl groups, the method for producing a multisubstituted biphenyl compound according to the present embodiment may further comprise a step of dehydrating the carboxyl groups. The dehydrating step allows to bond the above two R bonding to adjacent carbon atoms to each other to convert to an anhydride. For example, in the case of 3,3',4,4'-tetraalkylbiphenyl, the oxidation of the alkyl groups enables the derivatization thereof to 3,3',4,4'-biphenyltetracarboxylic acid and/or 3,3',4,4'-biphenyltetracarboxylic dianhydride. Moreover, further dehydration of 3,3',4,4'-biphenyltetracarboxylic acid enables the derivatization thereof to 3,3',4,4'-biphenyltetracarboxylic dianhydride.

The above oxidizing step can be performed by using a method such as those described in WO2012/046857 or WO2012/157749. In the oxidizing step, it is preferable to oxidize with a molecular oxygen a multisubstituted biphenyl compound in which R in the compound represented by formula (1) is an alkyl group, preferably in the presence of a metal compound containing at least one metal selected from the group consisting of cobalt, manganese and zirconium, and an imide compound such as N-hydroxyphthalimide.

Further, the above hydrolysis and dehydration can be performed by using a method such as those described in Japanese Patent No. 4048689 and Japanese Patent No. 4977989. It is preferable to perform the hydrolysis by adding only pure water and heating under an increased pressure. It is preferable to perform the dehydration by stirring while heating at 180 to 195° C. under an inert gas atmosphere.

Note that the obtained multisubstituted biphenyl compound may have a plurality of isomers. In this case, it is only necessary to appropriately separate them by using filtration, recrystallization and/or distillation, etc., and use for applications to be required. 3,3',4,4'-biphenyltetracarboxylic dianhydride is a useful compound as a raw material for polyimides.

EXAMPLES

Next, the present invention will be described specifically referring to Examples, however, the scope of the present invention is not limited thereto.

[Methods for Measuring Average Primary Particle Diameter of Support and Solid Catalyst and Average Particle Diameter of Gold Particles]

Primary particles of a support and a solid catalyst and gold particles on the support were observed by using TEM, and the diameter of a circle circumscribing their particle (circumcircle) in the TEM image was measured, and the diameters of them were defined as the primary particle diameters of the support and the solid catalyst and the particle diameter of the gold particle on the support, respectively. The particle diameters of arbitrarily selected ten or more particles were measured to determine the particle diameter distribution, and therewith the number-average diameters of the support, the solid catalyst and the gold particles on the support were calculated. The calculated number-average diameters were defined as the average primary particle diameters of the support and the solid catalyst and the average particle diameter of the gold particles, respectively. In addition, energy dispersive X-ray spectroscopy (EDS) measurement was performed for the TEM image and thereby the gold particle on the support was identified.

[Method for Measuring Amount of Immobilized Gold in Solid Catalyst]

A solid catalyst was heated to be dissolved in aqua regia and diluted with ultrapure water. The emission intensity of the gold dissolved in the solution was measured by using inductively coupled plasma-atomic emission spectroscopy (ICP-AES). The dissolved amount of the gold in the solution was calculated through comparing the emission intensity of the gold dissolved in the solution with that of gold in a standard solution with a known gold concentration. The gold content contained in a unit mass of the solid catalyst, i.e., the amount of the immobilized gold (% by mass) was calculated from the dissolved amount.

[Method for Identifying Product and Measuring Amount of Product]

Unless otherwise noted, identification of a reaction product and measurement of the amount of the product was performed with a gas chromatography (FID detector) through comparing the retention times and peak intensities between the reaction product and a standard substance. The measurement conditions are as follows.

Apparatus: Agilent 6850 Series II from Agilent Technologies

Column: HP-1 (inner diameter: 0.32 mm; length: 30 m; membrane thickness: 0.25 μm) from J&W Scientific Carrier gas: helium, 120 kPa Temperature-raising conditions: raised from 40° C. to 280° C. at 10° C./min and retained at 280° C. for 10 min.

[Method for Calculating Yield and Production Ratio]

For example, in the case that dimethyl o-phthalate is used as a substituted benzene compound (substrate), the following two products are present as the major isomers in the product (biphenyltetracarboxylic acid tetramethyl ester). Hereinafter, 3,3',4,4'-biphenyltetracarboxylic acid tetramethyl ester is sometimes referred to as "s-DM" (s-form) and 2,3,3',4'-biphenyltetraacetic acid tetramethyl ester as "a-DM" (a-form).

[Chemical Formula 14]

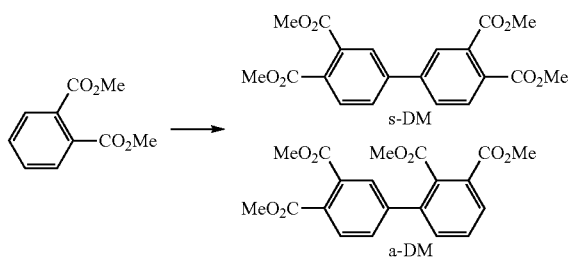

In the case that xylene is used as a substrate, the products are 3,3',4,4'-tetramethylbiphenyl (s-form) and 2,3,3',4'-tetramethylbiphenyl (a-form).

When the molar number of dimethyl o-phthalate used for the coupling is defined as $M_f$, and the molar numbers of produced s-DM and a-DM as $M_s$ and $M_a$, respectively, the yield of the product and the production ratio of s-DM to a-DM can be determined using the following formulae, respectively.

Yield (mol %)=$2 \times M_s \times 100/M_f$

Production ratio (s/a ratio)=$M_s/M_a$

[Method for Determining Equivalent Number of Solid Catalyst]

The equivalent number (mol % of gold immobilized onto a support relative to a substrate) in the case that a coupling reaction is performed by using a metal oxide ($Me_yO_z$) as a support was calculated using the following formula.

Equivalent number of solid catalyst (mol %)=$(100 \times b \times c)/\{d \times (a/y \times e + b \times 197)\}$ Me: metal element of support
O: oxygen atom
y, z: numerical values indicating numbers of Me and O in metal oxide, respectively
a: molar number (mol) of metal oxide constituting support used in preparing solid catalyst
b: molar number (mol) of gold compound used in preparing solid catalyst
c: mass (g) of solid catalyst used in coupling reaction
d: molar number (mol) of substrate used in coupling reaction
e: molar mass (g) of metal oxide ($Me_yO_z$)

Example 1-1

Synthesis of Solid Catalyst with Gold Immobilized onto Cobalt Oxide (Hereinafter, Also Referred to as "Au/$Co_3O_4$")

In 200 mL of distilled water were dissolved 5.52 g of cobalt (II) nitrate hexahydrate and 0.41 g of tetrachloroauric acid tetrahydrate at a room temperature (Aqueous Solution 1). Meanwhile, apart from this, 2.63 g of sodium carbonate was dissolved in 200 mL of distilled water (Aqueous Solution 2). The Aqueous Solution 1 was then added to the Aqueous Solution 2 at one time, and the mixture solution was stirred at a room temperature for 3 hours. The produced precipitate was washed with distilled water until its pH became constant and filtered. The residue was dried at 70° C. overnight. After drying, the residue was calcined in air at 300° C. for 4 hours to yield a solid catalyst with gold immobilized onto cobalt oxide (Au/$Co_3O_4$). The average primary particle diameter of the obtained solid catalyst was approximately 15 nm, the amount of the immobilized gold was 10% by mass, and the average particle diameter of the gold particles on the support was 2 nm.

Example 1-2

Synthesis of Solid Catalyst with Gold Immobilized onto Nickel Oxide (Hereinafter, Also Referred to as "Au/NiO")

In 200 mL of distilled water were dissolved 5.53 g of nickel nitrate hexahydrate and 0.41 g of tetrachloroauric acid tetrahydrate at a room temperature and heated to 70° C. (Aqueous Solution 3). Meanwhile, apart from this, 2.67 g of sodium carbonate was dissolved in 250 mL of distilled water and heated to 70° C. (Aqueous Solution 4). The Aqueous Solution 3 was then added to the Aqueous Solution 4 at one time, and the mixture solution was stirred at 70° C. for 1 hour. The produced precipitate was washed with distilled water until its pH became constant and filtered. The residue was dried at 70° C. overnight. After drying, the residue was calcined in air at 300° C. for 4 hours to yield a solid catalyst with gold immobilized onto nickel oxide (Au/NiO). The average primary particle diameter of the obtained solid catalyst was approximately 5 nm, the amount of the immobilized gold was 10% by mass, and the average particle diameter of the gold particles on the support was 4 nm.

Example 1-3

Synthesis of Solid Catalyst with Gold Immobilized onto Iron Oxide (Hereinafter, Also Referred to as "Au/$Fe_2O_3$")

In 200 mL of distilled water were dissolved 7.68 g of iron (II) nitrate nonahydrate and 0.41 g of tetrachloroauric acid tetrahydrate at a room temperature (Aqueous Solution 5). Meanwhile, apart from this, 3.88 g of sodium carbonate was dissolved in 370 mL of distilled water and heated to 70° C. (Aqueous Solution 6). The Aqueous Solution 5 was then added to the Aqueous Solution 6 at one time, and the mixture solution was stirred at 70° C. for 1 hour. The produced precipitate was washed with distilled water until its pH became constant and filtered. The residue was dried at 80° C. overnight. After drying, the residue was calcined in air at 300° C. for 4 hours to yield a solid catalyst with gold immobilized onto iron oxide (Au/$Fe_2O_3$). The average primary particle diameter of the obtained solid catalyst was approximately 20 nm, the amount of the immobilized gold was 9% by mass, and the average particle diameter of the gold particles on the support was 4 nm.

Example 1-4

Synthesis of Solid Catalyst with Gold Immobilized onto Cerium Oxide (Hereinafter, Also Referred to as "Au/$CeO_2$")

In 155 mL of distilled water was dissolved 64 mg of tetrachloroauric acid tetrahydrate and an aqueous solution of sodium hydroxide was added dropwise thereto while heating to 70° C. to adjust the pH of the solution to 7. To this was added 3 g of cerium oxide (Cerium Oxide HS (product name), from DAIICHI KIGENSO KAGAKU KOGYO CO., LTD., average particle diameter: 5 μm, average primary particle diameter: 8 nm), and thereafter stirred at 70° C. After 1 hour, the precipitate was washed with distilled water until its pH became constant and filtered. The residue was dried at 80° C. overnight. After drying, the residue was calcined in air at 300° C. for 4 hours to yield a solid catalyst with gold immobilized onto cerium oxide ($Au/CeO_2$). The average primary particle diameter of the obtained solid catalyst was approximately 8 nm, the amount of the immobilized gold was 0.8% by mass, and the average particle diameter of the gold particles on the support was 4 nm.

Example 1-5

Synthesis of Solid Catalyst with Gold Immobilized onto Titanium Oxide (Hereinafter, Also Referred to as "$Au/TiO_2$")

In 52 mL of distilled water was dissolved 22 mg of tetrachloroauric acid tetrahydrate and an aqueous solution of sodium hydroxide was added dropwise thereto while heating to 70° C. to adjust the pH of the solution to 7. To this was added 1 g of titanium oxide (P-25 (product name), from NIPPON AEROSIL CO., LTD., average primary particle diameter: 25 nm), and thereafter stirred at 70° C. After 1 hour, the precipitate was washed with distilled water until its pH became constant and filtered. The residue was dried at 100° C. overnight. After drying, the residue was calcined in air at 300° C. for 4 hours to yield a solid catalyst with gold immobilized onto titanium oxide ($Au/TiO_2$). The average primary particle diameter of the obtained solid catalyst was approximately 25 nm, the amount of the immobilized gold was 0.8% by mass, and the average particle diameter of the gold particles on the support was 3 nm.

Example 1-6

Synthesis of Solid Catalyst with Gold and Cobalt Immobilized onto Silica (Hereinafter, Also Referred to as "$Au/Co/SiO_2$")

In 10 mL of distilled water was dissolved 0.50 g of cobalt (II) nitrate hexahydrate, and 0.85 g of silica (CARiACT Q-15 (product name), from FUJI SILYSIA CHEMICAL LTD., average primary particle diameter: 75 to 150 μm) was added thereto followed by adding 0.11 g of tetrachloroauric acid tetrahydrate. Aqueous ammonia was added dropwise thereto while stirring at a room temperature to adjust the pH of the solution to 8.5. After stirring at a room temperature for 1 hour, the precipitate was washed with distilled water and filtered. The residue was dried at 120° C. for 20 hours. After drying, the residue was calcined in air at 400° C. for 5 hours to yield a solid catalyst with gold and cobalt immobilized onto silica ($Au/Co/SiO_2$). The average primary particle diameter of the obtained solid catalyst was approximately 100 van, and the amount of the immobilized gold was 4% by mass.

Example 1-7

Synthesis of Solid Catalyst with Gold Immobilized onto Cobalt Oxide-Cerium Oxide (Hereinafter, Also Referred to as "$Au/Co_3O_4$—$CeO_2$")

In 51 mL of distilled water was dissolved 21 mg of tetrachloroauric acid tetrahydrate and an aqueous solution of sodium hydroxide was added dropwise to adjust the pH of the solution to 7.6. To this was added 1 g of cobalt oxide-cerium oxide (complex oxide of cobalt oxide and cerium oxide, average primary particle diameter: 40 nm), stirred at 70° C. for 1 h, and thereafter the precipitate was washed with distilled water until its pH became constant and filtered. The residue was dried at 70° C. overnight. After drying, the residue was calcined in air at 300° C. for 4 hours to yield a solid catalyst with gold immobilized onto cobalt oxide-cerium oxide ($Au/Co_3O_4$—$CeO_2$). The average primary particle diameter of the obtained solid catalyst was approximately 40 nm, and the amount of the immobilized gold was 0.7% by mass.

Example 1-8

Synthesis of Solid Catalyst with Gold Immobilized onto Manganese Dioxide (Hereinafter, Also Referred to as "$Au/MnO_2$")

In 180 mL of distilled water was dissolved 110 mg of tetrachloroauric acid tetrahydrate, and 3.2 g of urea and 1 g of manganese dioxide (average primary particle diameter: 40 nm) were added thereto in this order at a room temperature. Thereafter, the solution was warmed gradually to 90° C. and stirred while heating at 90° C. for 18 hours. The precipitate was washed with distilled water and filtered. The obtained residue was dried at 65° C. overnight. After drying, the residue was calcined in air at 300° C. for 4 hours to yield a solid catalyst with gold immobilized onto manganese dioxide ($Au/MnO_2$). The average primary particle diameter of the obtained solid catalyst was approximately 40 nm, the amount of the immobilized gold was 4% by mass, and the average particle diameter of the gold particles on the support was 5 nm.

Example 1-9

Synthesis of Solid Catalyst with Gold Immobilized onto Zirconium Oxide (Hereinafter, Also Referred to as "$Au/ZrO_2$")

In 52 mL of distilled water was dissolved 22 mg of tetrachloroauric acid tetrahydrate and an aqueous solution of sodium hydroxide was added dropwise thereto while heating the solution to 70° C. to adjust the pH of the solution to 7. To the adjusted solution was added 1 g of zirconium oxide (RC-100 (product name), from DAIICHI KIGENSO KAGAKU KOGYO CO., LTD., average primary particle diameter: 5 nm), and thereafter stirred at 70° C. After 1 hour, the precipitate was washed with distilled water until its pH became constant and filtered. The residue was dried at 80° C. overnight. After drying, the residue was calcined in air at 300° C. for 4 hours to yield a solid catalyst with gold immobilized onto zirconium oxide ($Au/ZrO_2$). The average primary particle diameter of the obtained solid catalyst was approximately 5 nm, the amount of the immobilized gold was 1% by mass, and the average particle diameter of the gold particles on the support was 4 nm.

Reference Example 1-10

Preparation of Cobalt Oxide

Cobalt Oxide was obtained by calcining 11 g of basic cobalt carbonate in air at 300° C. for 4 hours.

Reference Example 1-11

Preparation of Cobalt Oxide

In 200 mL of distilled water was dissolved 5.82 g of cobalt (II) nitrate hexahydrate (Aqueous Solution 7). Meanwhile, apart from this, 2.63 g of sodium carbonate was dissolved in 200 mL of distilled water (Aqueous Solution 8). The Aqueous Solution 7 was then added to the Aqueous Solution 8 at one time, and the mixture solution was stirred at a room temperature for 3 hours. The produced precipitate was washed with distilled water until its pH became constant and filtered. The residue was dried at 70° C. overnight. After drying, the residue was calcined in air at 300° C. for 4 hours to yield cobalt oxide. The average primary particle diameter of the obtained cobalt oxide was approximately 15 nm.

Example 1-12

Synthesis of Solid Catalyst with Gold Immobilized onto Cobalt Oxide (Hereinafter, Also Referred to as "Au/$Co_3O_4$")

In 66 mL of distilled water was dissolved 470 mg of tetrachloroauric acid tetrahydrate, and 2.0 g of the cobalt oxide prepared in Reference Example 1-10 was added thereto at a room temperature, and stirred at a room temperature while adjusting its pH to 7 by adding an aqueous solution of sodium hydroxide dropwise. After 3 h, the precipitate was washed with distilled water and filtered. The obtained residue was dried at 65° C. overnight. After drying, the residue was calcined in air at 300° C. for 4 hours to yield a solid catalyst with gold immobilized onto cobalt oxide (Au/$Co_3O_4$) by using the deposition-precipitation method. The amount of the immobilized gold of the obtained solid catalyst was 7% by mass.

Example 1-13

Synthesis of Solid Catalyst with Gold Immobilized onto Lanthanum Oxide (Hereinafter, Also Referred to as "Au/$La_2O_3$")

In 200 mL of distilled water were dissolved 8.2 g of lanthanum (III) nitrate hexahydrate and 0.41 g of tetrachloroauric acid tetrahydrate at a room temperature (Aqueous Solution 9). Meanwhile, apart from this, 3.9 g of sodium carbonate was dissolved in 366 mL of distilled water (Aqueous Solution 10). The Aqueous Solution 9 was then added to the Aqueous Solution 10 at one time, and the mixture solution was stirred at 70° C. for 1.5 hours. The produced precipitate was washed with distilled water until its pH became constant and filtered. The residue was dried at 80° C. overnight. After drying, the residue was calcined in air at 300° C. for 4 hours to yield a solid catalyst with gold immobilized onto lanthanum oxide (Au/$La_2O_3$). The amount of the immobilized gold of the obtained solid catalyst was 6% by mass.

Example 1-14

Synthesis of Solid Catalyst with Gold Immobilized onto Aluminum Oxide (Hereinafter, Also Referred to as "Au/$Al_2O_3$")

In 100 mL of distilled water were dissolved 173 mg of tetrachloroauric acid tetrahydrate and 25 g of urea, and 1.0 g of aluminum oxide (AKP-G015 (product name), from Sumitomo Chemical Co., Ltd., particle diameter: less than 100 nm) was added to this solution at a room temperature. Thereafter, the solution was warmed gradually to 80° C. and stirred while heating at 80° C. for 8 hours. After cooled to 50° C., the precipitate was washed with distilled water 5 times and filtered. The obtained residue was dried at 80° C. overnight. After drying, the residue was calcined in air at 300° C. for 4 hours to yield a solid catalyst with gold immobilized onto aluminum oxide (Au/$Al_2O_3$). The primary particle diameter of the obtained solid catalyst was less than 100 nm, and the amount of the immobilized gold was 8% by mass.

Example 1-15

Synthesis of Solid Catalyst with Gold Immobilized onto Zirconium Oxide (Hereinafter, Also Referred to as "Au/$ZrO_2$")

In 100 mL of distilled water were dissolved 173 mg of tetrachloroauric acid tetrahydrate and 25 g of urea, and 1.0 g of zirconium oxide (RC-100 (product name), from DAI-ICHI KIGENSO KAGAKU KOGYO CO., LTD., average primary particle diameter: 5 nm) was added to this solution at a room temperature. Thereafter, the solution was warmed gradually to 80° C. and stirred while heating at 80° C. for 8 hours. After cooled to 50° C., the precipitate was washed with distilled water 5 times and filtered. The obtained residue was dried at 80° C. overnight. After drying, the residue was calcined in air at 300° C. for 4 hours to yield a solid catalyst with gold immobilized onto zirconium oxide (Au/$ZrO_2$). The average primary particle diameter of the obtained solid catalyst was approximately 5 nm, and the amount of the immobilized gold was 8% by mass.

Example 1-16

Synthesis of Solid Catalyst with Gold Immobilized onto Zirconium Oxide (Hereinafter, Also Referred to as "Au/$ZrO_2$")

In 100 mL of distilled water were dissolved 173 mg of tetrachloroauric acid tetrahydrate and 2.5 g of urea, and 1.0 g of zirconium oxide (RC-100 (product name), from DAI-ICHI KIGENSO KAGAKU KOGYO CO., LTD., average primary particle diameter: 5 nm) was added to this solution at a room temperature. Thereafter, the solution was warmed gradually to 90° C. and stirred while heating at 90° C. for 4 hours. After cooled to a room temperature, the precipitate was washed with distilled water 5 times and filtered. The obtained residue was dried at 70° C. overnight. After drying, the residue was calcined in air at 300° C. for 4 hours to yield a solid catalyst with gold immobilized onto zirconium oxide (Au/$ZrO_2$). The average primary particle diameter of the obtained solid catalyst was approximately 5 nm, and the amount of the immobilized gold was 8% by mass.

Example 1-17

Synthesis of Solid Catalyst with Gold Immobilized onto Titanium Oxide (Hereinafter, Also Referred to as "Au/$TiO_2$")

In 100 mL of distilled water were dissolved 173 mg of tetrachloroauric acid tetrahydrate and 25 g of urea, and 1.0 g of titanium oxide (P-25 (product name), from NIPPON AEROSIL CO., LTD., average primary particle diameter: 25 nm) was added to this solution at a room temperature. Thereafter, the solution was warmed gradually to 80° C. and stirred while heating at 80° C. for 8 hours. After cooled to 50° C., the precipitate was washed with distilled water 5 times and filtered. The obtained residue was dried at 80° C. overnight. After drying, the residue was calcined in air at 300° C. for 4 hours to yield a solid catalyst with gold immobilized onto titanium oxide ($Au/TiO_2$). The average primary particle diameter of the obtained solid catalyst was approximately 25 nm, and the amount of the immobilized gold was 8% by mass.

Example 1-18

Synthesis of Solid Catalyst with Gold Immobilized onto Cerium Oxide (Hereinafter, Also Referred to as "$Au/CeO_2$")

In 100 mL of distilled water were dissolved 173 mg of tetrachloroauric acid tetrahydrate and 25 g of urea, and 1.0 g of cerium oxide (JRC-CEO-3 (product name), from DAIICHI KIGENSO KAGAKU KOGYO CO., LTD., average primary particle diameter: 11 nm) was added to this solution at a room temperature. Thereafter, the solution was warmed gradually to 80° C. and stirred while heating at 80° C. for 8 hours. After cooled to 50° C., the precipitate was washed with distilled water 5 times and filtered. The obtained residue was dried at 80° C. overnight. After drying, the residue was calcined in air at 300° C. for 4 hours to yield a solid catalyst with gold immobilized onto cerium oxide ($Au/CeO_2$). The average primary particle diameter of the obtained solid catalyst was approximately 11 nm, and the amount of the immobilized gold was 8% by mass.

Example 1-19

Synthesis of Solid Catalyst with Gold Immobilized onto Cerium Oxide (Hereinafter, Also Referred to as "$Au/CeO_2$")

In 100 mL of distilled water were dissolved 173 mg of tetrachloroauric acid tetrahydrate and 25 g of urea, and 1.0 g of cerium oxide (Cerium Oxide HS (product name), from DAIICHI KIGENSO KAGAKU KOGYO CO., LTD., average primary particle diameter: 8 nm) was added to this solution at a room temperature. Thereafter, the solution was warmed gradually to 80° C. and stirred while heating at 80° C. for 8 hours. After cooled to 50° C., the precipitate was washed with distilled water 5 times and filtered. The obtained residue was dried at 80° C. overnight. After drying, the residue is packed in a U-shaped reaction tube, and heated to 200° C. while running a hydrogen gas at 18 mL/min for 4 hours to yield a solid catalyst with gold immobilized onto cerium oxide ($Au/CeO_2$). The average primary particle diameter of the obtained solid catalyst was approximately 8 nm, and the amount of the immobilized gold was 8% by mass.

Example 1-20

Synthesis of Solid Catalyst with Gold Immobilized onto Manganese Sesquioxide (Hereinafter, Also Referred to as "$Au/Mn_2O_3$")

In 360 mL of distilled water was dissolved 220 mg of tetrachloroauric acid tetrahydrate, and 6.4 g of urea and 2 g of manganese sesquioxide (from Sigma-Aldrich Japan K.K., average primary particle diameter: 40 nm) were added to this solution in this order at a room temperature. Thereafter, the solution was warmed gradually to 90° C. and stirred while heating at 90° C. for 18 hours. The precipitate was washed with distilled water and filtered. The obtained residue was dried at 65° C. overnight. After drying, the residue was calcined in air at 300° C. for 4 hours to yield a solid catalyst with gold immobilized onto manganese sesquioxide ($Au/Mn_2O_3$). The average primary particle diameter of the obtained solid catalyst was approximately 40 nm, the amount of the immobilized gold was 4% by mass, and the average particle diameter of the gold particles on the support was 9 nm.

Reference Example 1-21

Preparation of Manganese Dioxide

In 50 mL of distilled water was dissolved 3 g of manganese sulfate hydrate and this solution was warmed to 85° C. A solution with 8.1 g of ammonium peroxodisulfate dissolved in 50 mL of distilled water was added gradually to the warmed solution and stirred at 85° C. After 6 hours, the obtained precipitate was washed with distilled water and filtered. The obtained residue was dried at 65° C. to yield manganese dioxide ($MnO_2$). The X-ray diffraction (XRD) pattern of the obtained manganese dioxide is shown in FIG. 3.

Example 1-22

Synthesis of Solid Catalyst with Gold Immobilized onto Manganese Dioxide (Hereinafter, Also Referred to as "$Au/MnO_2$")

In 360 mL of distilled water was dissolved 220 mg of tetrachloroauric acid tetrahydrate and 6.4 g of urea and 2 g of the manganese dioxide prepared in Reference Example 1-21 were added thereto in this order at a room temperature. Thereafter, the reaction solution was warmed gradually to 90° C. and stirred while heating at 90° C. for 18 hours. The precipitate was washed with distilled water and filtered. The obtained residue was dried at 65° C. overnight. After drying, the residue was calcined in air at 300° C. for 4 hours to yield a solid catalyst with gold immobilized onto manganese dioxide ($Au/MnO_2$). The amount of the immobilized gold of the obtained solid catalyst was 5% by mass.

Reference Example 1-23

Preparation of Lanthanum-Doped Cerium Oxide (Hereinafter, Also Referred to as "$Ce(La)O_2$")

In 200 mL of distilled water were dissolved 12 g of ammonium hexanitratocerate (IV), 1.1 g of lanthanum nitrate hexahydrate and 24 g of urea, and this solution was stirred under reflux. After 8 hours, the precipitate was washed with distilled water and filtered. The residue was dried at 80° C. After drying, the residue was calcined in air at 400° C. for 7 hours to yield a lanthanum-doped cerium oxide ($Ce(La)O_2$). The average primary particle diameter of the obtained lanthanum-doped cerium oxide was 4 nm.

Reference Example 1-24

Preparation of Zirconium-Doped Cerium Oxide
(Hereinafter, Also Referred to as "Ce(Zr)O$_2$")

In 200 mL of distilled water were dissolved 12 g of ammonium hexanitratocerate (IV), 0.7 g of zirconium nitrate and 24 g of urea, and this solution was stirred under reflux. After 8 hours, the precipitate was washed with distilled water and filtered. The residue was dried at 80° C. After drying, the residue was calcined in air at 400° C. for 7 hours to yield a zirconium-doped cerium oxide (Ce(Zr)O$_2$). The average primary particle diameter of the obtained zirconium-doped cerium oxide was 4 nm.

Example 1-25

Synthesis of Solid Catalyst with Gold Immobilized onto Lanthanum-Doped Cerium Oxide (Hereinafter, Also Referred to as "Au/Ce(La)O$_2$")

In 100 mL of distilled water was dissolved 43 mg of tetrachloroauric acid tetrahydrate, and an aqueous solution of sodium hydroxide was added dropwise thereto while warming to 70° C., to adjust the pH of the solution to 7 to 8. To this was added 1 g of the Ce(La)O$_2$ prepared in Reference Example 1-23, and thereafter stirred at 70° C. After 1 hour, the precipitate was washed with distilled water until its pH became constant and filtered. The residue was dried at 80° C. overnight. After drying, the residue was calcined in air at 300° C. for 4 hours. The residue was further reduced under hydrogen at 300° C. to yield a solid catalyst with gold immobilized onto lanthanum-doped cerium oxide (Au/Ce(La)O$_2$). The average primary particle diameter of the obtained solid catalyst was 4 nm, the amount of the immobilized gold was 1% by mass, and the average particle diameter of the gold particles on the support was 3 nm.

Example 1-26

Synthesis of Solid Catalyst with Gold Immobilized onto Zirconium-Doped Cerium Oxide (Hereinafter, Also Referred to as "Au/Ce(Zr)O$_2$")

In 100 mL of distilled water was dissolved 43 mg of tetrachloroauric acid tetrahydrate, and an aqueous solution of sodium hydroxide was added dropwise thereto while warming to 70° C., to adjust the pH of the solution to 7 to 8. To this was added 1 g of the Ce(Zr)O$_2$ prepared in Reference Example 1-24, and thereafter stirred at 70° C. After 1 hour, the precipitate was washed with distilled water until its pH became constant and filtered. The residue was dried at 80° C. overnight. After drying, the residue was calcined in air at 300° C. for 4 hours. The residue was further reduced under hydrogen at 300° C. to yield a solid catalyst with gold immobilized onto zirconium-doped cerium oxide (Au/Ce(Zr)O$_2$). The average primary particle diameter of the obtained solid catalyst was 4 nm, the amount of the immobilized gold was 1% by mass, and the average particle diameter of the gold particles on the support was 3 nm.

Example 1-27

Reactivation of Catalyst

To a three-necked flask with an internal volume of 25 mL were introduced 3.5 g (18 mmol) of dimethyl o-phthalate, 1.9 g (6 mol % relative to dimethyl o-phthalate) of the Au/Co$_3$O$_4$ prepared in Example 1-1 and 7 mL of acetic acid. The reactor vessel was soaked in an oil bath preset at 125° C. to allow to react for 72 hours followed by an analysis and as the result it was found that 3,3',4,4'-biphenyltetracarboxylic acid tetramethyl ester (s-DM) had been produced in a yield of 11%. After further reaction for 24 hours, the yield was still 11%, from which it was confirmed that the reaction had stopped. The precipitation was filtered and the residue was washed with acetone. The washed residue was dried at 100° C. under a reduced pressure to yield a solid catalyst with gold immobilized onto cobalt oxide (Au/Co$_3$O$_4$). The solid was burned in air at 300° C. for 4 hours to yield a burned solid catalyst (Au/Co$_3$O$_4$). The particle diameter of the obtained solid catalyst was 5 to 20 nm, and the average particle diameter of the gold particles on the support was 8 nm.

Example 2-1

Synthesis of Biphenyltetracarboxylic Acid Ester

To a SUS autoclave (internal volume: 50 mL) equipped with an inner glass tube were introduced 0.27 g (1.4 mmol) of dimethyl o-phthalate, 0.10 g (4 mol % relative to dimethyl o-phthalate) of the Au/Co$_3$O$_4$ prepared in Example 1-1 and 2.7 mL of acetic acid. Thereafter, an air was pressed thereinto so that the pressure in the reaction system became 2.5 MPa. The autoclave was then soaked in an oil bath preset at 150° C. to allow to react for 18 hours. After the reaction finished, the autoclave was water-cooled, and the gas was released from the inner glass tube. The obtained reaction solution was analyzed with a gas chromatography and as the result it was found that 3,3',4,4'-biphenyltetracarboxylic acid tetramethyl ester (s-DM) had been produced in a yield of 20% (s/a ratio=10).

Example 2-2

Synthesis of Biphenyltetracarboxylic Acid Ester

To a SUS autoclave (internal volume: 50 mL) equipped with an inner glass tube were introduced 0.23 g (1.2 mmol) of dimethyl o-phthalate, 0.15 g (7 mol % relative to dimethyl o-phthalate) of the Au/Co$_3$O$_4$ prepared in Example 1-1 and 0.8 mL of acetic acid. After the gas in the reaction system was replaced with a nitrogen gas, a nitrogen gas was pressed thereinto so that the pressure in the reaction system became 1.0 MPa. The autoclave was then soaked in an oil bath preset at 150° C. to allow to react for 18 hours. After the reaction finished, the autoclave was water-cooled, and the gas was released from the inner glass tube. The obtained reaction solution was analyzed with a gas chromatography and as the result it was found that 3,3',4,4'-biphenyltetracarboxylic acid tetramethyl ester (s-DM) had been produced in a yield of 21% (s/a ratio=7).

Example 2-3

Synthesis of Biphenyltetracarboxylic Acid Ester

To a SUS autoclave (internal volume: 50 mL) equipped with an inner glass tube were introduced 2.78 g (14.3 mmol) of dimethyl o-phthalate and 26 mg (0.1 mol % relative to dimethyl o-phthalate) of the Au/Co$_3$O$_4$ prepared in Example 1-1. An air was pressed thereinto so that the pressure in the reaction system became 2.5 MPa. The autoclave was then soaked in an oil bath preset at 150° C. to allow to react for 40 hours. Further, the oil bath was heat to 200° C. to allow to react for 20 hours. After the reaction finished, the autoclave was water-cooled, and the gas was released from the inner glass tube. The obtained reaction solution was analyzed with a gas chromatography and as the result it was found that 3,3',4,4'-biphenyltetracarboxylic acid tetramethyl ester (s-DM) had been produced in a yield of 1% (s/a ratio=2).

Example 2-4

Synthesis of Biphenyltetracarboxylic Acid Ester)

To a SUS autoclave (internal volume: 30 mL) equipped with an inner glass tube were introduced 0.20 g (1.0 mmol) of dimethyl o-phthalate, 74 mg (4 mol % relative to dimethyl o-phthalate) of the Au/Co$_3$O$_4$ prepared in Example 1-1 and 0.4 mL of a mixture solution of acetic acid and dioxane (acetic acid:dioxane=1:1 (volume ratio)). An oxygen gas was pressed thereinto so that the pressure in the reaction system became 1.5 MPa. The autoclave was then soaked in an oil bath preset at 150° C. to allow to react for 18 hours. After the reaction finished, the autoclave was air-cooled, and the gas was released from the inner glass tube. The obtained reaction solution was analyzed with a gas chromatography and as the result it was found that 3,3',4,4'-biphenyltetracarboxylic acid tetramethyl ester (s-DM) had been produced in a yield of 25% (s/a ratio=13).

Example 2-5

Synthesis of Biphenyltetracarboxylic Acid Ester

To a SUS autoclave (internal volume: 30 mL) equipped with an inner glass tube were introduced 0.20 g (1.0 mmol) of dimethyl o-phthalate, 74 mg (4 mol % relative to dimethyl o-phthalate) of the Au/Co$_3$O$_4$ prepared in Example 1-1 and 0.5 mL of butyric acid. An oxygen gas was pressed thereinto so that the pressure in the reaction system became 1.5 MPa. The autoclave was then soaked in an oil bath preset at 150° C. to allow to react for 18 hours. After the reaction finished, the autoclave was air-cooled, and the gas was released from the inner glass tube. The obtained reaction solution was analyzed with a gas chromatography and as the result it was found that 3,3',4,4'-biphenyltetracarboxylic acid tetramethyl ester (s-DM) had been produced in a yield of 11% (s/a ratio=6).

Example 2-6

Synthesis of Biphenyltetracarboxylic Acid Ester

To a SUS autoclave (internal volume: 30 mL) equipped with an inner glass tube were introduced 0.20 g (1.0 mmol) of dimethyl o-phthalate, 74 mg (4 mol % relative to dimethyl o-phthalate) of the Au/Co$_3$O$_4$ prepared in Example 1-1 and 0.5 mL of isovaleric acid. An oxygen gas was pressed thereinto so that the pressure in the reaction system became 1.5 MPa. The autoclave was then soaked in an oil bath preset at 150° C. to allow to react for 18 hours. After the reaction finished, the autoclave was air-cooled, and the gas was released from the inner glass tube. The obtained reaction solution was analyzed with a gas chromatography and as the result it was found that 3,3',4,4'-biphenyltetracarboxylic acid tetramethyl ester (s-DM) had been produced in a yield of 2% (s/a ratio=100).

Example 2-7

Synthesis of Biphenyltetracarboxylic Acid Ester

To a glass Schlenk flask with an internal volume of 10 mL were introduced 0.20 g (1.0 mmol) of dimethyl o-phthalate, 74 mg (4 mol % relative to dimethyl o-phthalate) of the Au/Co$_3$O$_4$ prepared in Example 1-1 and 0.4 mL of propionic acid. After the gas in the reaction system was replaced with a nitrogen gas at a normal pressure, the Schlenk flask was soaked in an oil bath preset at 150° C. to allow to react for 34 hours. After the reaction finished, the Schlenk flask was air-cooled, and the gas in the Schlenk flask was released. The obtained reaction solution was analyzed with a gas chromatography and as the result it was found that 3,3',4,4'-biphenyltetracarboxylic acid tetramethyl ester (s-DM) had been produced in a yield of 5% (s/a ratio=4).

Example 2-8

Synthesis of Biphenyltetracarboxylic Acid Ester

To a glass Schlenk flask with an internal volume of 10 mL were introduced 0.20 g (1.0 mmol) of dimethyl o-phthalate, 73 mg (4 mol % relative to dimethyl o-phthalate) of the Au/Co$_3$O$_4$ prepared in Example 1-1 and 0.4 mL of acetic acid. After the gas in the reaction system was replaced with a nitrogen gas at a normal pressure, the Schlenk flask was soaked in an oil bath preset at 125° C. to allow to react for 67 hours. After the reaction finished, the Schlenk flask was air-cooled, and the gas in the Schlenk flask was released. The obtained reaction solution was analyzed with a gas chromatography and as the result it was found that 3,3',4,4'-biphenyltetracarboxylic acid tetramethyl ester (s-DM) had been produced in a yield of 22% (s/a ratio=13).

Example 2-9

Synthesis of Biphenyltetracarboxylic Acid Ester

To a SUS autoclave (internal volume: 30 mL) equipped with an inner glass tube were introduced 0.20 g (1.0 mmol) of dimethyl o-phthalate, 100 mg (6 mol % relative to dimethyl o-phthalate) of the Au/NiO prepared in Example 1-2 and 0.4 mL of acetic acid. An oxygen gas was pressed thereinto so that the pressure in the reaction system became 1.5 MPa. The autoclave was then soaked in an oil bath preset at 150° C. to allow to react for 18 hours. After the reaction finished, the autoclave was air-cooled, and the gas was released from the inner glass tube. The obtained reaction solution was analyzed with a gas chromatography and as the result it was found that 3,3',4,4'-biphenyltetracarboxylic acid tetramethyl ester (s-DM) had been produced in a yield of 11% (s/a ratio=3).

Example 2-10

Synthesis of Biphenyltetracarboxylic Acid Ester

To a SUS autoclave (internal volume: 30 mL) equipped with an inner glass tube were introduced 0.20 g (1.0 mmol) of dimethyl o-phthalate, 70 mg (4 mol % relative to dimethyl o-phthalate) of the Au/Fe$_2$O$_3$ prepared in Example 1-3 and 0.4 mL of acetic acid. An oxygen gas was pressed thereinto so that the pressure in the reaction system became 1.5 MPa. The autoclave was then soaked in an oil bath preset at 150° C. to allow to react for 18 hours. After the reaction finished, the autoclave was air-cooled, and the gas was released from the inner glass tube. The obtained reaction solution was analyzed with a gas chromatography and as the result it was found that 3,3',4,4'-biphenyltetracarboxylic acid tetramethyl ester (s-DM) had been produced in a yield of 6% (s/a ratio=6).

Example 2-11

Synthesis of Biphenyltetracarboxylic Acid Ester

To a SUS autoclave (internal volume: 30 mL) equipped with an inner glass tube were introduced 0.20 g (1.0 mmol) of dimethyl o-phthalate, 0.15 g (0.8 mol % relative to dimethyl o-phthalate) of the $Au/CeO_2$ prepared in Example 1-4 and 0.5 mL of acetic acid. An oxygen gas was pressed thereinto so that the pressure in the reaction system became 1.5 MPa. The autoclave was then soaked in an oil bath preset at 150° C. to allow to react for 18 hours. After the reaction finished, the autoclave was air-cooled, and the gas was released from the inner glass tube. The obtained reaction solution was analyzed with a gas chromatography and as the result it was found that 3,3',4,4'-biphenyltetracarboxylic acid tetramethyl ester (s-DM) had been produced in a yield of 17% (s/a ratio=4).

Example 2-12

Synthesis of Biphenyltetracarboxylic Acid Ester

To a SUS autoclave (internal volume: 30 mL) equipped with an inner glass tube were introduced 0.20 g (1.0 mmol) of dimethyl o-phthalate, 0.15 g (0.8 mol % relative to dimethyl o-phthalate) of the $Au/TiO_2$ prepared in Example 1-5 and 0.4 mL of acetic acid. An oxygen gas was pressed thereinto so that the pressure in the reaction system became 1.5 MPa. The autoclave was then soaked in an oil bath preset at 150° C. to allow to react for 18 hours. After the reaction finished, the autoclave was air-cooled, and the gas was released from the inner glass tube. The obtained reaction solution was analyzed with a gas chromatography and as the result it was found that 3,3',4,4'-biphenyltetracarboxylic acid tetramethyl ester (s-DM) had been produced in a yield of 2% (s/a ratio=2).

Example 2-13

Synthesis of Biphenyltetracarboxylic Acid Ester

To a SUS autoclave (internal volume: 30 mL) equipped with an inner glass tube were introduced 0.20 g (1.0 mmol) of dimethyl o-phthalate, 0.20 g (5 mol % relative to dimethyl o-phthalate) of the $Au/Co/SiO_2$ prepared in Example 1-6 and 0.4 mL of acetic acid. An oxygen gas was pressed thereinto so that the pressure in the reaction system became 1.5 MPa. The autoclave was then soaked in an oil bath preset at 150° C. to allow to react for 18 hours. After the reaction finished, the autoclave was air-cooled, and the gas was released from the inner glass tube. The obtained reaction solution was analyzed with a gas chromatography and as the result it was found that 3,3',4,4'-biphenyltetracarboxylic acid tetramethyl ester (s-DM) had been produced in a yield of 13% (s/a ratio=3).

Example 2-14

Synthesis of Biphenyltetracarboxylic Acid Ester

To a SUS autoclave (internal volume: 30 mL) equipped with an inner glass tube were introduced 0.20 g (1.0 mmol) of dimethyl o-phthalate, 0.40 g (2 mol % relative to dimethyl o-phthalate) of the $Au/Co_3O_4$—$CeO_2$ prepared in Example 1-7 and 0.7 mL of acetic acid. An oxygen gas was pressed thereinto so that the pressure in the reaction system became 1.5 MPa. The autoclave was then soaked in an oil bath preset at 150° C. to allow to react for 18 hours. After the reaction finished, the autoclave was air-cooled, and the gas was released from the inner glass tube. The obtained reaction solution was analyzed with a gas chromatography and as the result it was found that 3,3',4,4'-biphenyltetracarboxylic acid tetramethyl ester (s-DM) had been produced in a yield of 1% (s/a ratio=100).

Example 2-15

Synthesis of Biphenyltetracarboxylic Acid Ester

To a SUS autoclave (internal volume: 30 mL) equipped with an inner glass tube were introduced 0.20 g (1.0 mmol) of dimethyl o-phthalate, 0.15 g (0.8 mol % relative to dimethyl o-phthalate) of the $Au/ZrO_2$ prepared in Example 1-9 and 0.5 mL of acetic acid. An oxygen gas was pressed thereinto so that the pressure in the reaction system became 1.5 MPa. The autoclave was then soaked in an oil bath preset at 150° C. to allow to react for 18 hours. After the reaction finished, the autoclave was air-cooled, and the gas was released from the inner glass tube. The obtained reaction solution was analyzed with a gas chromatography and as the result it was found that 3,3',4,4'-biphenyltetracarboxylic acid tetramethyl ester (s-DM) had been produced in a yield of 21% (s/a ratio=7).

Example 2-16

Synthesis of Biphenyltetracarboxylic Acid Ester

To a SUS autoclave (internal volume: 30 mL) equipped with an inner glass tube were introduced 0.20 g (1 mmol) of dimethyl o-phthalate, 0.15 g (0.75 mol % relative to dimethyl o-phthalate) of the $Au/Co_3O_4$—$CeO_2$ prepared in Example 1-7 and 0.5 mL of acetic acid. An oxygen gas was pressed thereinto so that the pressure in the reaction system became 1.5 MPa. The autoclave was then soaked in an oil bath preset at 150° C. to allow to react for 18 hours. After the reaction finished, the autoclave was air-cooled, and the gas was released from the inner glass tube. The obtained reaction solution was analyzed with a gas chromatography and as the result it was found that 3,3',4,4'-biphenyltetracarboxylic acid tetramethyl ester (s-DM) had been produced in a yield of 27% (s/a ratio=14).

Example 2-17

Synthesis of Biphenyltetracarboxylic Acid Ester

To a glass reactor vessel with an internal volume of 30 mL were introduced 0.20 g (1.0 mmol) of dimethyl o-phthalate, 70 mg (4 mol % relative to dimethyl o-phthalate) of the $Au/Co_3O_4$ prepared in Example 1-12 by using the deposition-precipitation method and 0.4 mL of acetic acid. The reaction vessel was contacted with an aluminum block preset at 125° C. under air at a normal pressure to allow to react for 24 hours. After the reaction finished, the reaction solution was air-cooled. The obtained reaction solution was analyzed with a gas chromatography and as the result it was found that 3,3',4,4'-biphenyltetracarboxylic acid tetramethyl ester (s-DM) had been produced in a yield of 12% (s/a ratio=10).

Example 2-18

Synthesis of Biphenyltetracarboxylic Acid Ester

To a SUS autoclave (internal volume: 30 mL) equipped with an inner glass tube were introduced 0.20 g (1.0 mmol) of dimethyl o-phthalate, 0.13 g (4 mol % relative to dimethyl o-phthalate) of the $Au/La_2O_3$ prepared in Example 1-13 and 0.5 mL of acetic acid. An oxygen gas was pressed thereinto so that the pressure in the reaction system became 1.5 MPa. The autoclave was then soaked in an oil bath preset at 150° C. to allow to react for 18 hours. After the reaction finished, the autoclave was air-cooled, and the gas was released from the inner glass tube. The obtained reaction solution was analyzed with a gas chromatography and as the result it was found that 3,3',4,4'-biphenyltetracarboxylic acid tetramethyl ester (s-DM) had been produced in a yield of 3% (s/a ratio=3).

Example 2-19

Synthesis of Biphenyltetracarboxylic Acid Ester

To a SUS autoclave (internal volume: 30 mL) equipped with an inner glass tube were introduced 0.20 g (1 mmol) of dimethyl o-phthalate, 0.10 g (4 mol % relative to dimethyl o-phthalate) of the $Au/Al_2O_3$ prepared in Example 1-14 and 0.5 mL of acetic acid. An oxygen gas was pressed thereinto so that the pressure in the reaction system became 1.6 MPa. The autoclave was then soaked in an oil bath preset at 150° C. to allow to react for 18 hours. After the reaction finished, the autoclave was air-cooled, and the gas was released from the inner glass tube. The obtained reaction solution was analyzed with a gas chromatography and as the result it was found that 3,3',4,4'-biphenyltetracarboxylic acid tetramethyl ester (s-DM) had been produced in a yield of 23% (s/a ratio=5).

Example 2-20

Synthesis of Biphenyltetracarboxylic Acid Ester

To a SUS autoclave (internal volume: 30 mL) equipped with an inner glass tube were introduced 0.20 g (1 mmol) of dimethyl o-phthalate, 0.10 g (4 mol % relative to dimethyl o-phthalate) of the $Au/ZrO_2$ prepared in Example 1-15 and 0.5 mL of acetic acid. An oxygen gas was pressed thereinto so that the pressure in the reaction system became 1.85 MPa. The autoclave was then soaked in an oil bath preset at 150° C. to allow to react for 18 hours. After the reaction finished, the autoclave was air-cooled, and the gas was released from the inner glass tube. The obtained reaction solution was analyzed with a gas chromatography and as the result it was found that 3,3',4,4'-biphenyltetracarboxylic acid tetramethyl ester (s-DM) had been produced in a yield of 45% (s/a ratio=8).

Example 2-21

Synthesis of Biphenyltetracarboxylic Acid Ester

To a SUS autoclave (internal volume: 30 mL) equipped with an inner glass tube were introduced 0.20 g (1 mmol) of dimethyl o-phthalate, 0.10 g (4 mol % relative to dimethyl o-phthalate) of the $Au/ZrO_2$ prepared in Example 1-16 and 0.5 mL of acetic acid. An oxygen gas was pressed thereinto so that the pressure in the reaction system became 1.85 MPa. The autoclave was then soaked in an oil bath preset at 140° C. to allow to react for 48 hours. After the reaction finished, the autoclave was air-cooled, and the gas was released from the autoclave. The obtained reaction solution was analyzed with a gas chromatography and as the result it was found that 3,3',4,4'-biphenyltetracarboxylic acid tetramethyl ester (s-DM) had been produced in a yield of 58% (s/a ratio=15).

Example 2-22

Synthesis of Biphenyltetracarboxylic Acid Ester

To a SUS autoclave (internal volume: 30 mL) equipped with an inner glass tube were introduced 0.20 g (1 mmol) of dimethyl o-phthalate, 0.10 g (4 mol % relative to dimethyl o-phthalate) of the $Au/TiO_2$ prepared in Example 1-17 and 0.5 mL of acetic acid. An oxygen gas was pressed thereinto so that the pressure in the reaction system became 1.6 MPa. The autoclave was then soaked in an oil bath preset at 150° C. to allow to react for 72 hours. After the reaction finished, the autoclave was air-cooled, and the gas was released from the inner glass tube. The obtained reaction solution was analyzed with a gas chromatography and as the result it was found that 3,3',4,4'-biphenyltetracarboxylic acid tetramethyl ester (s-DM) had been produced in a yield of 31% (s/a ratio=4).

Example 2-23

Synthesis of Biphenyltetracarboxylic Acid Ester

To a SUS autoclave (internal volume: 30 mL) equipped with an inner glass tube were introduced 0.20 g (1 mmol) of dimethyl o-phthalate, 0.10 g (4 mol % relative to dimethyl o-phthalate) of the $Au/CeO_2$ prepared in Example 1-18 and 0.5 mL of acetic acid. An oxygen gas was pressed thereinto so that the pressure in the reaction system became 1.6 MPa. The autoclave was then soaked in an oil bath preset at 150° C. to allow to react for 18 hours. After the reaction finished, the autoclave was air-cooled, and the gas was released from the inner glass tube. The obtained reaction solution was analyzed with a gas chromatography and as the result it was found that 3,3',4,4'-biphenyltetracarboxylic acid tetramethyl ester (s-DM) had been produced in a yield of 28% (s/a ratio=7).

Example 2-24

Synthesis of Biphenyltetracarboxylic Acid Ester

To a SUS autoclave (internal volume: 30 mL) equipped with an inner glass tube were introduced 0.20 g (1 mmol) of dimethyl o-phthalate, 0.10 g (4 mol % relative to dimethyl o-phthalate) of the $Au/CeO_2$ prepared in Example 1-19 and 0.5 mL of acetic acid. An oxygen gas was pressed thereinto so that the pressure in the reaction system became 1.5 MPa. The autoclave was then soaked in an oil bath preset at 150° C. to allow to react for 18 hours. After the reaction finished, the autoclave was air-cooled, and the gas was released from the autoclave. The obtained reaction solution was analyzed with a gas chromatography and as the result it was found that 3,3',4,4'-biphenyltetracarboxylic acid tetramethyl ester (s-DM) had been produced in a yield of 25% (s/a ratio=7).

Example 2-25

Synthesis of Biphenyltetracarboxylic Acid Ester

To a glass reactor vessel with an internal volume of 30 mL were introduced 0.20 g (1.0 mmol) of dimethyl o-phthalate, 0.21 g (6 mol % relative to dimethyl o-phthalate) of the Au/Mn$_2$O$_3$ prepared in Example 1-20 by using the deposition-precipitation method and 0.4 mL of acetic acid. The reactor vessel was contacted with an aluminum block preset at 125° C. under air at a normal pressure to allow to react. Thereto was added 0.21 g (6 mol % relative to dimethyl o-phthalate) of the Au/Mn$_2$O$_3$ at 140 hours and 207 hours after the initiation of the reaction, respectively, to allow to react for 279 hours in total from the initiation of the reaction. After the reaction finished, the reaction solution was air-cooled. The obtained reaction solution was analyzed with a gas chromatography and as the result it was found that 3,3',4,4'-biphenyltetracarboxylic acid tetramethyl ester (s-DM) had been produced in a yield of 58% (s/a ratio=20).

Example 2-26

Synthesis of Biphenyltetracarboxylic Acid Ester

To a glass reactor vessel with an internal volume of 30 mL were introduced 0.20 g (1.0 mmol) of dimethyl o-phthalate, 71 mg (4 mol % relative to dimethyl o-phthalate) of the Au/MnO$_2$ prepared in Example 1-22 by using the deposition-precipitation method and 0.4 mL of acetic acid. The reactor vessel was contacted with an aluminum block preset at 125° C. under air at a normal pressure to allow to react for 48 hours. After the reaction finished, the reaction solution was air-cooled. The obtained reaction solution was analyzed with a gas chromatography and as the result it was found that 3,3',4,4'-biphenyltetracarboxylic acid tetramethyl ester (s-DM) had been produced in a yield of 17% (s/a ratio=28).

Example 2-27

Synthesis of Biphenyltetracarboxylic Acid Ester with Reactivated Solid Catalyst

To a glass reactor vessel with an internal volume of 30 mL were introduced 0.10 g (0.5 mmol) of dimethyl o-phthalate, 36 mg (4 mol % relative to dimethyl o-phthalate) of the Au/Co$_3$O$_4$ calcined in Example 1-27 and 0.2 mL, of acetic acid. The reactor vessel was contacted with an aluminum block preset at 125° C. under air at a normal pressure to allow to react for 41 hours. After the reaction finished, the reaction solution was air-cooled. The obtained reaction solution was analyzed with a gas chromatography and as the result it was found that 3,3',4,4'-biphenyltetracarboxylic acid tetramethyl ester (s-DM) had been produced in a yield of 7% (s/a ratio=15).

Example 2-28

Synthesis of Biphenyltetracarboxylic Acid Ester

To a glass reactor vessel with an internal volume of 2 mL were introduced 0.40 g (2.1 mmol) of dimethyl o-phthalate and 0.141 g (4 mol % relative to dimethyl o-phthalate) of the Au/Co$_3$O$_4$ prepared in Example 1-12 by using the deposition-precipitation method. The reactor vessel was soaked in an oil bath preset at 150° C. under air at a normal pressure to allow to react for 24 hours. After the reaction finished, the reaction solution obtained after air-cooling was analyzed with a gas chromatography and as the result it was found that 3,3',4,4'-biphenyltetracarboxylic acid tetramethyl ester (s-DM) had been produced in a yield of 9% (s/a ratio=2).

Example 2-29

Synthesis of Biphenyltetracarboxylic Acid Ester

To a glass reactor vessel with an internal volume of 2 mL were introduced 0.41 g (2.1 mmol) of dimethyl o-phthalate and 0.142 g (4 mol % relative to dimethyl o-phthalate) of the Au/Co$_3$O$_4$ prepared in Example 1-1 by using the coprecipitation method. The reactor vessel was soaked in an oil bath preset at 200° C. under air at a normal pressure to allow to react for 24 hours. After the reaction finished, the reaction solution obtained after air-cooling was analyzed with a gas chromatography and as the result it was found that 3,3',4,4'-biphenyltetracarboxylic acid tetramethyl ester (s-DM) had been produced in a yield of 1% (s/a ratio=2).

Example 2-30

Synthesis of Biphenyltetracarboxylic Acid Ester

To a glass reactor vessel with an internal volume of 2 mL were introduced 0.40 g (2.1 mmol) of dimethyl o-phthalate and 0.144 g (4 mol % relative to dimethyl o-phthalate) of the Au/Co$_3$O$_4$ prepared in Example 1-12 by using the deposition-precipitation method. The reactor vessel was soaked in an oil bath preset at 200° C. under air at a normal pressure to allow to react for 24 hours. After the reaction finished, the reaction solution obtained after air-cooling was analyzed with a gas chromatography and as the result it was found that 3,3',4,4'-biphenyltetracarboxylic acid tetramethyl ester (s-DM) had been produced in a yield of 8% (s/a ratio=2).

Example 2-31

Synthesis of Biphenyltetracarboxylic Acid Ester

To a glass reactor vessel with an internal volume of 30 mL were introduced 0.21 g (1.1 mmol) of dimethyl o-phthalate, 84 mg (0.4 mol % relative to dimethyl o-phthalate) of the Au/Ce(La)O$_2$ prepared in Example 1-25 and 0.4 mL of acetic acid. The reactor vessel was contacted with an aluminum block preset at 125° C. under air at a normal pressure to allow to react for 100 hours. After the reaction finished, the reaction solution obtained after air-cooling was analyzed with a gas chromatography and as the result it was found that 3,3',4,4'-biphenyltetracarboxylic acid tetramethyl ester (s-DM) had been produced in a yield of 9% (s/a ratio=15).

Example 2-32

Synthesis of Biphenyltetracarboxylic Acid Ester

To a glass reactor vessel with an internal volume of 30 mL were introduced 0.21 g (1.1 mmol) of dimethyl o-phthalate, 84 mg (0.4 mol % relative to dimethyl o-phthalate) of the Au/Ce(Zr)O$_2$ prepared in Example 1-26 and 0.4 mL of acetic acid. The reactor vessel was contacted with an aluminum block preset at 125° C. under air at a normal pressure to allow to react for 48 hours. After the reaction finished, the reaction solution obtained after air-cooling was analyzed with a gas chromatography and as the result it was found that 3,3',4,4'-biphenyltetracarboxylic acid tetramethyl ester (s-DM) had been produced in a yield of 1% (s/a ratio=9).

Example 2-33

Synthesis of Biphenyltetracarboxylic Acid Ester

To a SUS autoclave (internal volume: 10 mL) not equipped with an inner glass tube were introduced 0.20 g (1.0 mmol) of dimethyl o-phthalate, 85 mg (0.4 mol % of gold relative to dimethyl o-phthalate) of the $Au/TiO_2$ prepared in Example 1-5 and 0.2 mL of 1H,1H-tridecafluoro-1-heptanol. An air was pressed thereinto so that the pressure in the reaction system became 2.5 MPa. The autoclave was then soaked in an oil bath preset at 150° C. to allow to react for 24 hours. After the reaction finished, the autoclave was air-cooled, and the gas was released. The obtained reaction solution was analyzed with a gas chromatography and as the result it was found that 3,3',4,4'-biphenyltetracarboxylic acid tetramethyl ester (s-DM) had been produced in a yield of 1% (s/a ratio=1).

Example 2-34

Synthesis of Biphenyltetracarboxylic Acid Ester

To a SUS autoclave (internal volume: 10 mL) not equipped with an inner glass tube were introduced 0.20 g (1.0 mmol) of dimethyl o-phthalate, 72 mg (4 mol % of gold relative to dimethyl o-phthalate) of the $Au/Co_3O_4$ prepared in Example 1-1 and 0.3 mL of 1H,1H-tridecafluoro-1-heptanol. An air was pressed thereinto so that the pressure in the reaction system became 2.5 MPa. The autoclave was then soaked in an oil bath preset at 150° C. to allow to react for 16 hours. After the reaction finished, the autoclave was air-cooled, and the gas was released. The obtained reaction solution was analyzed with a gas chromatography and as the result it was found that 3,3',4,4'-biphenyltetracarboxylic acid tetramethyl ester (s-DM) had been produced in a yield of 1% (s/a ratio=1).

Example 2-35

Synthesis of 3,3',4,4'-Tetramethyl biphenyl

To a SUS autoclave (internal volume: 50 mL) equipped with an inner glass tube were introduced 0.11 g (1.0 mmol) of o-xylene, 72 mg (4 mol % relative to o-xylene) of the $Au/Co_3O_4$ prepared in Example 1-1 and 0.4 mL of acetic acid. After the gas in the reaction system was replaced with a nitrogen gas, a nitrogen gas was pressed thereinto so that the pressure in the reaction system became 0.5 MPa. The autoclave was then soaked in an oil bath preset at 125° C. to allow to react for 24 hours. After the reaction finished, the autoclave was water-cooled, and the gas was released from the inner glass tube. The obtained reaction solution was analyzed with a gas chromatography and as the result it was found that 3,3',4,4'-tetramethylbiphenyl had been produced in a yield of 3.2%.

Example 2-36

Synthesis of 3,3',4,4'-Tetramethyl biphenyl

To a reactor vessel with an internal volume of 5 mL equipped with a stirrer and refluxing apparatus were introduced 0.11 g (1.0 mmol) of o-xylene, 72 mg (4 mol % relative to o-xylene) of the $Au/Co_3O_4$ prepared in Example 1-1 and 0.4 mL of acetic acid. After the gas in the reaction system was replaced with a nitrogen gas, the reaction proceeded for 51 hours with a nitrogen balloon installed and with the heated part preset at 125° C. After the reaction finished, the reaction solution obtained after air-cooling was analyzed with a gas chromatography and as the result it was found that 3,3',4,4'-tetramethylbiphenyl had been produced in a yield of 7.5%.

Example 2-37

Synthesis of Dimethyl 4,4'-biphenyldicarboxylate

To a reactor vessel with an internal volume of 5 mL equipped with a stirrer and refluxing apparatus were introduced 0.14 g (1.0 mmol) of methyl benzoate, 72 mg (4 mol % relative to methyl benzoate) of the $Au/Co_3O_4$ prepared in Example 1-1 and 0.4 mL of acetic acid. After the gas in the reaction system was replaced with a nitrogen gas, the reaction proceeded for 51 hours with a nitrogen balloon installed and with the heated part preset at 125° C. After the reaction finished, the reaction solution obtained after air-cooling was analyzed with a gas chromatography and as the result it was found that dimethyl 4,4'-biphenyldicarboxylate had been produced in a yield of 3.3%.

Example 2-38

Synthesis of 4,4'-Dimethylbiphenyl

To a SUS autoclave (internal volume: 50 mL) equipped with an inner glass tube were introduced 0.09 g (1.0 mmol) of toluene, 72 mg (4 mol % relative to toluene) of the $Au/Co_3O_4$ prepared in Example 1-1 and 0.4 mL of acetic acid. After the gas in the reaction system was replaced with a nitrogen gas, a nitrogen gas was pressed thereinto so that the pressure in the reaction system became 0.5 MPa. The autoclave was then soaked in an oil bath preset at 125° C. to allow to react for 25 hours. After the reaction finished, the autoclave was water-cooled, and the gas was released from the inner glass tube. The obtained reaction solution was analyzed with a gas chromatography. FIG. 1 shows the chart of gas chromatography. In the chart of gas chromatography (FIG. 1), six peaks each corresponding to a dimer of toluene (dimethylbiphenyl) were observed, and among them, the peak observed at a position of a retention time of 15.9 min was the peak of 4,4'-dimethylbiphenyl.

Example 2-39

Synthesis of Benzoic Acid Dimer

Figure 2:
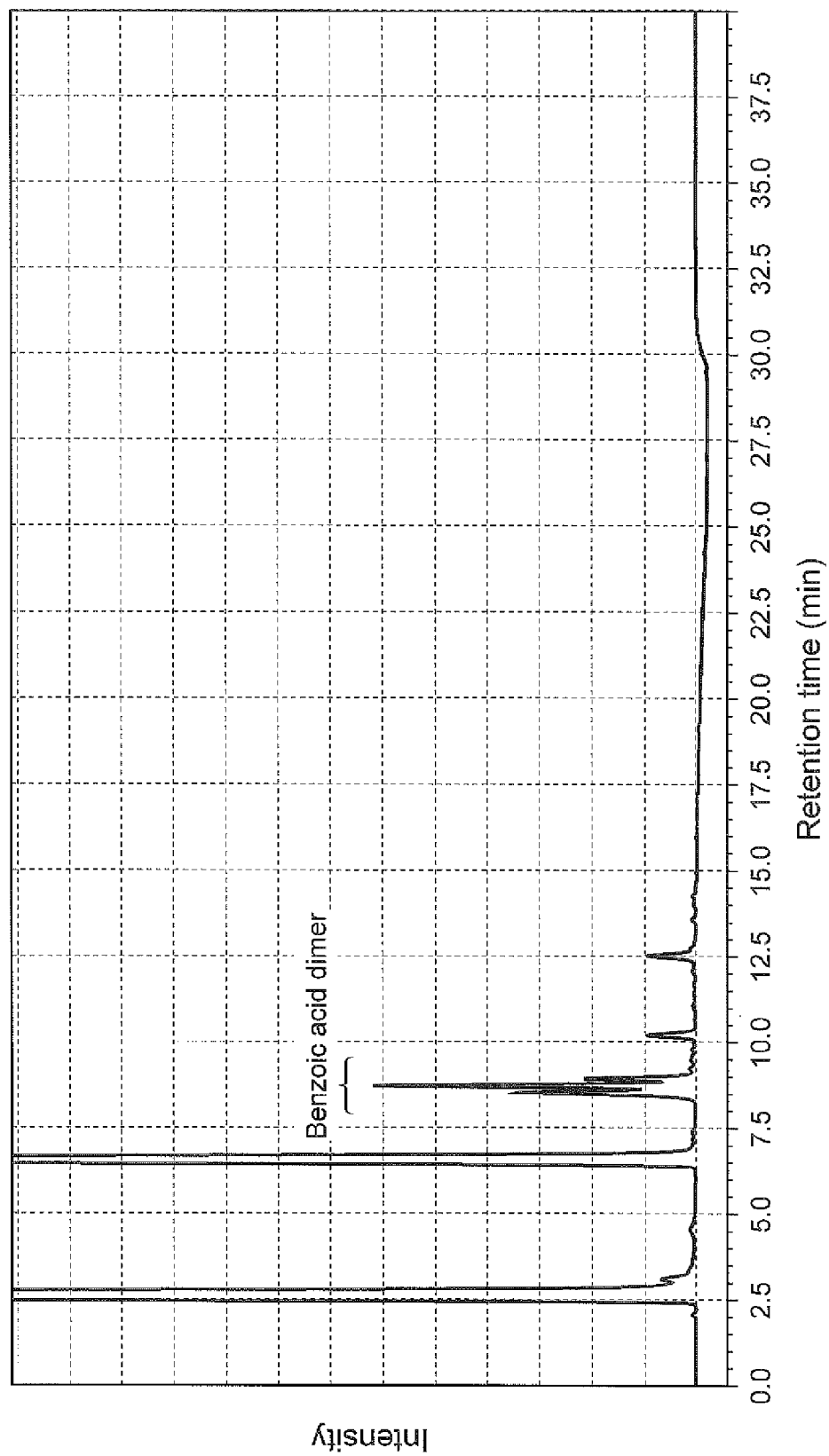
FIG. 2 is a chart of high-performance liquid chromatography (HPLC) for a reaction solution obtained in Example 2-39.

To a reactor vessel with an internal volume of 5 mL equipped with a stirrer and refluxing apparatus were introduced 0.12 g (1.0 mmol) of benzoic acid, 72 mg (4 mol % relative to benzoic acid) of the $Au/Co_3O_4$ prepared in Example 1-1 and 0.4 mL of acetic acid. After the gas in the reaction system was replaced with a nitrogen gas, the reaction proceeded for 51 hours with a nitrogen balloon installed and with the heated part preset at 125° C. After the reaction finished, the reaction solution obtained after air-cooling was analyzed with a high-performance liquid chromatography (HPLC). FIG. 2 shows the chart of HPLC. The peaks at retention times of 8.5 min, 8.7 min and 8.9 min were analyzed with HPLC/MS and as the result it was confirmed that each of the peaks was the peak corresponding to the molecular weight of a benzoic acid dimer.

The measurement conditions for HPLC were as follows:
Apparatus: LC-20AB from Shimadzu Corporation
Column: Waters Atlantis dC18 5 μm ϕ4.6×150 mm
Eluent: A: 0.1% HCOOH aqueous solution, B: CH$_3$CN
Time program: 0.01 min: A/B=70/30, 20.00 min: A/B=5195, 25.00 min: A/B=5/95, 25.01 min: A/B=70/30, 40.00 min: A/B=70/30
Flow rate: 1 mL/min
Detector: 254 nm Example 2-40

Synthesis of Tetramethylbiphenyl

To a SUS autoclave (internal volume: 50 mL) equipped with an inner glass tube were introduced 0.52 g (4.9 mmol) of xylene (a mixture of o-, m- and p-form thereof) and 0.15 g (0.8 mol % relative to xylene) of the Au/MnO$_2$ prepared in Example 1-8. An oxygen gas was pressed thereinto so that the pressure in the reaction system became 0.5 MPa. The autoclave was then soaked in an oil bath preset at 100° C. to allow to react for 19 hours. After the reaction finished, the autoclave was air-cooled, and the gas was released from the inner glass tube. The obtained reaction solution was analyzed with a gas chromatography and as the result it was confirmed that xylene dimers (tetramethylbiphenyl) had been produced.

Example 2-41

Synthesis of Tetramethylbiphenyl

To a Pyrex (Registered Trademark) glass vial with an internal volume of 13 mL were introduced 0.11 g (1 mmol) of o-xylene, 74 mg (4 mol % relative to o-xylene) of the Au/Co$_3$O$_4$ prepared in Example 1-1 and 0.5 mL of acetic acid. The reactor vessel was soaked in an oil bath preset at 130° C. under air at a normal pressure to allow to react for 18 hours. After the reaction finished, the reaction solution was air-cooled. The obtained reaction solution was analyzed with a gas chromatography and as the result it was found that 3,3',4,4'-tetramethylbiphenyl had been produced in a yield of 13% (s/a ratio=7).

Example 2-42

Synthesis of 4,4'-Bistrifluoromethylbiphenyl

To a SUS autoclave (internal volume: 30 mL) equipped with an inner glass tube were introduced 0.15 g (1 mmol) of trifluoromethylbenzene, 74 mg (4 mol % relative to trifluoromethylbenzene) of the Au/Co$_3$O$_4$ prepared in Example 1-1 and 0.5 mL of acetic acid. An oxygen gas was pressed thereinto so that the pressure in the reaction system became 1.6 MPa. The autoclave was then soaked in an oil bath preset at 150° C. to allow to react for 18 hours. After the reaction finished, the autoclave was air-cooled, and the gas was released from the inner glass tube. The obtained reaction solution was analyzed with a gas chromatography and as the result it was found that 4,4'-bistrifluoromethylbiphenyl had been produced in a yield of 4%.

Example 2-43

Synthesis of 2,2',5,5'-Tetramethoxybiphenyl

To a Pyrex (Registered Trademark) glass vial with an internal volume of 13 mL were introduced 0.14 g (1 mmol) of p-dimethoxybenzene, 74 mg (4 mol % relative to p-dimethoxybenzene) of the Au/Co$_3$O$_4$ prepared in Example 1-1 and 0.5 mL of acetic acid. The reactor vessel was soaked in an oil bath preset at 150° C. under air at a normal pressure to allow to react for 18 hours. After the reaction finished, the reaction solution was air-cooled. The obtained reaction solution was analyzed with a gas chromatography and as the result it was found that 2,2',5,5'-tetramethoxybiphenyl had been produced in a yield of 21%.

Example 2-44

Synthesis of Di-tert-butylbiphenyl

To a SUS autoclave (internal volume: 30 mL) equipped with an inner glass tube were introduced 0.13 g (1 mmol) of tert-butylbenzene, 75 mg (4 mol % relative to tert-butylbenzene) of the Au/Co$_3$O$_4$ prepared in Example 1-1 and 0.5 mL of acetic acid. An oxygen gas was pressed thereinto so that the pressure in the reaction system became 1.6 MPa. The autoclave was then soaked in an oil bath preset at 150° C. to allow to react for 66 hours. After the reaction finished, the autoclave was air-cooled, and the gas was released from the inner glass tube. The obtained reaction solution was analyzed with a gas chromatography and as the result it was found that a mixture of 4,4'-di-tert-butylbiphenyl, 4,3'-di-tert-butylbiphenyl and 3,3'-di-tert-butylbiphenyl had been produced in a yield of 62% in total.

Example 2-45

Synthesis of 3,3',4,4'-Tetramethoxybiphenyl

To a glass reactor vessel with an internal volume of 30 mL were introduced 0.14 g (1.0 mmol) of o-dimethoxybenzene, 72 mg (4 mol % relative to o-dimethoxybenzene) of the Au/Co$_3$O$_4$ prepared in Example 1-1 and 0.4 mL of acetic acid. The reactor vessel was contacted with an aluminum block preset at 125° C. under air at a normal pressure to allow to react for 15 hours. After the reaction finished, the reaction solution was air-cooled. The obtained reaction solution was analyzed with a gas chromatography and as the result it was found that 3,3',4,4'-tetramethoxybiphenyl had been produced in a yield of 19%.

Example 2-46

Synthesis of 2,2',3,3',5,5'-Hexamethyl-[biphenyl]-4,4'-diol

To a glass reactor vessel with an internal volume of 30 mL were introduced 0.14 g (1.0 mmol) of 2,3,6-trimethylphenol, 72 mg (4 mol % relative to 2,3,6-trimethylphenol) of the Au/Co$_3$O$_4$ prepared in Example 1-1 and 0.4 mL of acetic acid. The reactor vessel was contacted with an aluminum block preset at 125° C. under air at a normal pressure to allow to react for 22 hours. After the reaction finished, the reaction solution was air-cooled. The obtained reaction solution was analyzed with a gas chromatography and as the result it was found that 2,2',3,3',5,5'-hexamethyl-[biphenyl]-4,4'-diol had been produced in a yield of 46%.

Comparative Example 2-1

Synthesis of Biphenyltetracarboxylic Acid Ester

To a glass Schlenk flask with an internal volume of 30 mL were introduced 0.21 g (1.1 mmol) of dimethyl o-phthalate, 24 mg (6 mol % relative to dimethyl o-phthalate) of tetrachloroauric acid tetrahydrate and 0.4 mL of acetic acid. The Schlenk flask was soaked in an oil bath preset at 125° C. to allow to react under air at a normal pressure for 20 hours. After the reaction finished, the Schlenk flask was air-cooled. The obtained reaction solution was analyzed with a gas chromatography and as the result it was found that 3,3',4,4'-biphenyltetracarboxylic acid tetramethyl ester had not been produced at all.

Comparative Example 2-2

Gold Elution Experiment

To a glass reactor vessel with an internal volume of 10 mL were introduced 75 mg of the Au/$Co_3O_4$ prepared in Example 1-1 and 0.4 mL of acetic acid. The reactor vessel was soaked in an oil bath preset at 125° C. under a nitrogen gas atmosphere at a normal pressure and stirred while heating for 1 hour. Immediate after stirring while heating, the solution was filtered while being hot and the residue was washed with 3 mL of acetic acid heated to 125° C. in advance. The obtained filtrate was analyzed by using ICP-AES and as the result it was found that Au was not detected.

Comparative Example 2-3

Synthesis of Di-Tert-Butylbiphenyl Using $Co_3O_4$ with No Gold Immobilized

To a SUS autoclave (internal volume: 30 mL) equipped with an inner glass tube were introduced 0.13 g (1 mmol) of tert-butylbenzene, 66 mg (0.27 mmol) of the $Co_3O_4$ prepared in Reference Example 1-11 and 0.5 mL of acetic acid. An oxygen gas was pressed thereinto so that the pressure in the reaction system became 1.6 MPa. The autoclave was then soaked in an oil bath preset at 150° C. to allow to react for 18 hours. After the reaction finished, the autoclave was air-cooled, and the gas was released from the inner glass tube. The obtained reaction solution was analyzed with a gas chromatography and as the result it was found that the yield of a multisubstituted biphenyl compound was 0%.

Comparative Example 2-4

Synthesis of 2,2',5,5'-Tetramethoxybiphenyl Using $Co_3O_4$ with No Gold Immobilized To a SUS autoclave (internal volume: 30 mL) equipped with an inner glass tube were introduced 0.14 g (1 mmol) of p-dimethoxybenzene, 66 mg (0.27 mmol) of the $Co_3O_4$ prepared in Reference Example 1-11 and 0.5 mL of acetic acid. An oxygen gas was pressed thereinto so that the pressure in the reaction system became 0.2 MPa. The autoclave was then soaked in an oil bath preset at 150° C. to allow to react for 18 hours. After the reaction finished, the autoclave was air-cooled, and the gas was released from the inner glass tube. The obtained reaction solution was analyzed with a gas chromatography and as the result it was found that the yield of a multisubstituted biphenyl compound was 0%.

Comparative Example 2-5

Synthesis of Tetramethylbiphenyl Using $Co_3O_4$ with No Gold Immobilized

To a Pyrex (Registered Trademark) glass vial with an internal volume of 13 mL were introduced 0.11 g (1 mmol) of o-xylene, 66 mg (0.27 mmol) of the $Co_3O_4$ prepared in Reference Example 1-11 and 0.5 mL of acetic acid. The reactor vessel was soaked in an oil bath preset at 150° C. under air at a normal pressure to allow to react for 18 hours. After the reaction finished, the reaction solution was air-cooled, and the obtained reaction solution was analyzed with a gas chromatography and as the result it was found that the yield of a multisubstituted biphenyl compound was 0%.

Example 3-1

Synthesis of 3,3',4,4'-Biphenyltetracarboxylic Dianhydride

To a titanium autoclave with an internal volume of 100 mL were introduced 2.10 g (10 mmol) of 3,3',4,4'-tetramethylbiphenyl synthesized in Example 2-15, 12.4 mg (0.05 mmol) of cobalt acetate tetrahydrate and 12.2 mg (0.05 mmol) of manganese acetate tetrahydrate, 163 mg (1 mmol) of N-hydroxyphthalimide (hereinafter, referred to as "NHPI") and 15 mL of acetic acid, and allowed to react under an air atmosphere (inner pressure: 3 MPa) at 150° C. The autoclave was cooled to a room temperature at 1 hour after the initiation of the reaction, and the gas in the autoclave was released. After further addition of 163 mg of NHPI into the autoclave, the reaction was restarted at 150° C. After 1 hour, these series of operations (cooling, release of gas, addition and restart of reaction) were repeated again and the reaction was performed for 3 hours in total. After the reaction finished, the autoclave was cooled to a room temperature and the gas in the autoclave was released. The solvent was distilled off from the obtained reaction solution, ethyl acetate and water were added thereto, the reaction solution was separated, and thereafter the ethyl acetate layer was washed with water to remove the metal compounds, yielding 3,3',4,4'-biphenyltetracarboxylic dianhydride.

The methods for producing and the results of the analyses for the solid catalysts or oxides obtained in the above Examples 1-1 to 1-9, 1-12 to 1-20, 1-22 and 1-25 to 1-27 and Reference Examples 1-10 to 1-11, 1-21 and 1-23 to 1-24 are summarized and shown in Table 1.

TABLE 1

| | Support or catalyst | Production method | Average primary particle diameter of solid catalyst (nm) | Amount of immobilized gold (% by mass) | Average particle diameter of gold particles (nm) |
|---|---|---|---|---|---|
| Example 1-1 | Au/$Co_3O_4$ | coprecipitation method | approx 15 | 10 | 2 |
| Example 1-2 | Au/NiO | coprecipitation method | approx 5 | 10 | 4 |
| Example 1-3 | Au/$Fe_2O_3$ | coprecipitation method | approx 20 | 9 | 4 |
| Example 1-4 | Au/$CeO_2$ | deposition-precipitation method | approx 8 | 0.8 | 4 |
| Example 1-5 | Au/$TiO_2$ | deposition-precipitation method | approx 25 | 0.8 | 3 |
| Example 1-6 | Au/Co/$SiO_2$ | deposition-precipitation method | approx 100 μm | 4 | — |
| Example 1-7 | Au/$Co_3O_4$—$CeO_2$ | deposition-precipitation method | approx 40 | 0.7 | — |

TABLE 1-continued

|  | Support or catalyst | Production method | Average primary particle diameter of solid catalyst (nm) | Amount of immobilized gold (% by mass) | Average particle diameter of gold particles (nm) |
|---|---|---|---|---|---|
| Example 1-8 | Au/MnO$_2$ | deposition-precipitation method | approx 40 | 4 | 5 |
| Example 1-9 | Au/ZrO$_2$ | deposition-precipitation method | approx 5 | 1 | 4 |
| Reference Example 1-10 | Co$_3$O$_4$ | — | — | — | — |
| Reference Example 1-11 | Co$_3$O$_4$ | — | approx 15 | — | — |
| Example 1-12 | Au/Co$_3$O$_4$ | deposition-precipitation method | — | 7 | — |
| Example 1-13 | Au/La$_2$O$_3$ | coprecipitation method | — | 6 | — |
| Example 1-14 | Au/Al$_2$O$_3$ | deposition-precipitation method | — | 8 | — |
| Example 1-15 | Au/ZrO$_2$ | deposition-precipitation method | approx 5 | 8 | — |
| Example 1-16 | Au/ZrO$_2$ | deposition-precipitation method | approx 5 | 8 | — |
| Example 1-17 | Au/TiO$_2$ | deposition-precipitation method | approx 25 | 8 | — |
| Example 1-18 | Au/CeO$_2$ | deposition-precipitation method | approx 11 | 8 | — |
| Example 1-19 | Au/CeO$_2$ | deposition-precipitation method | approx 8 | 8 | — |
| Example 1-20 | Au/Mn$_2$O$_3$ | deposition-precipitation method | approx 40 | 4 | 9 |
| Reference Example 1-21 | MnO$_2$ | — | — | — | — |
| Example 1-22 | Au/MnO$_2$ | deposition-precipitation method | — | 5 | — |
| Reference Example 1-23 | Ce(La)O$_2$ | — | approx 4 | — | — |
| Reference Example 1-24 | Ce(Zr)O$_2$ | — | approx 4 | — | — |
| Example 1-25 | Au/Ce(La)O$_2$ | deposition-precipitation method | approx 4 | 1 | 3 |
| Example 1-26 | Au/Ce(Zr)O$_2$ | deposition-precipitation method | approx 4 | 1 | 3 |
| Example 1-27 | Au/Co$_3$O$_4$ | reuse | — | — | 8 |

In addition, the conditions for the coupling reactions and the results of analyses for the products in Examples 2-1 to 2-47 and Comparative Examples 2-1 to 2-5 are summarized and shown in Tables 2 to 10. The numerical value given in a parenthesis in the column of Solid catalyst in Tables 2 to 9 indicates a ratio (an equivalent number of a solid catalyst) of the molar number of gold immobilized onto a support to the total molar number of a substituted benzene compound. In table 10, the numerical value given in a parenthesis for Tetrachloroauric acid tetrahydrate in Comparative Example 2-1 indicates a ratio of the molar number of tetrachloroauric acid tetrahydrate to the total molar number of a substituted benzene compound.

TABLE 2

|  |  | Example 2-1 | Example 2-2 | Example 2-3 | Example 2-4 | Example 2-5 | Example 2-6 |
|---|---|---|---|---|---|---|---|
| Substrate | dimethyl o-phthalate | 0.27 g | 0.23 g | 2.78 g | 0.20 g | 0.20 g | 0.20 g |
| Solid catalyst | Au/Co$_3$O$_4$ (Example 1-1) | 0.10 g (4 mol %) | 0.15 g (7 mol %) | 26 mg (0.1 mol %) | 74 mg (4 mol %) | 74 mg (4 mol %) | 74 mg (4 mol %) |
| Solvent | acetic acid | 2.7 mL | 0.8 mL | — | — | — | — |
|  | mixture solution (acetic acid/dioxane = 1:1 (v/v)) | — | — | — | 0.4 mL | — | — |
|  | butyric acid | — | — | — | — | 0.5 mL | — |
|  | isovaleric acid | — | — | — | — | — | 0.5 mL |
| Reaction conditions | atmosphere | air | nitrogen gas | air | oxygen gas | oxygen gas | oxygen gas |
|  | pressure (MPa) | 2.5 | 1.0 | 2.5 | 1.5 | 1.5 | 1.5 |
|  | temperature (° C.) | 150 | 150 | 150→200 | 150 | 150 | 150 |
| Result | yield (%) | 20 | 21 | 1 | 25 | 11 | 2 |
|  | s/a ratio | 10 | 7 | 2 | 13 | 6 | 100 |

TABLE 3

|  |  | Example 2-7 | Example 2-8 | Example 2-9 | Example 2-10 | Example 2-11 | Example 2-12 |
| --- | --- | --- | --- | --- | --- | --- | --- |
| Substrate | dimethyl o-phthalate | 0.20 g | 0.20 g | 0.20 g | 0.20 g | 0.20 g | 0.20 g |
| Solid catalyst | Au/Co$_3$O$_4$ (Example 1-1) | 74 mg (4 mol %) | 73 mg (4 mol %) | — | — | — | — |
|  | Au/NiO (Example 1-2) | — | — | 100 mg (6 mol %) | — | — | — |
|  | Au/Fe$_2$O$_3$ (Example 1-3) | — | — | — | 70 mg (4 mol %) | — | — |
|  | Au/CeO$_2$ (Example 1-4) | — | — | — | — | 0.15 g (0.8 mol %) | — |
|  | Au/TiO$_2$ (Example 1-5) | — | — | — | — | — | 0.15 g (0.8 mol %) |
| Solvent | propionic acid | 0.4 mL | — | — | — | — | — |
|  | acetic acid | — | 0.4 mL | 0.4 mL | 0.4 mL | 0.5 mL | 0.4 mL |
| Reaction conditions | atmosphere | nitrogen gas | nitrogen gas | oxygen gas | oxygen gas | oxygen gas | oxygen gas |
|  | pressure (MPa) | normal pressure | normal pressure | 1.5 | 1.5 | 1.5 | 1.5 |
|  | temperature (° C.) | 150 | 125 | 150 | 150 | 150 | 150 |
| Result | yield (%) | 5 | 22 | 11 | 6 | 17 | 2 |
|  | s/a ratio | 4 | 13 | 3 | 6 | 4 | 2 |

TABLE 4

|  |  | Example 2-13 | Example 2-14 | Example 2-15 | Example 2-16 | Example 2-17 | Example 2-18 |
| --- | --- | --- | --- | --- | --- | --- | --- |
| Substrate | dimethyl o-phthalate | 0.20 g | 0.20 g | 0.20 g | 0.20 g | 0.20 g | 0.20 g |
| Solid catalyst | Au/Co/SiO$_2$ (Example 1-6) | 0.20 g (5 mol %) | — | — | — | — | — |
|  | Au/Co$_3$O$_4$—CeO$_2$ (Example 1-7) | — | 0.40 g (2 mol %) | — | — | — | — |
|  | Au/ZrO$_2$ (Example 1-9) | — | — | 0.15 g (0.8 mol %) | — | — | — |
|  | Au/Co$_3$O$_4$—CeO$_2$ (Example 1-7) | — | — | — | 0.15 g (0.75 mol %) | — | — |
|  | Au/Co$_3$O$_4$ (Example 1-12) | — | — | — | — | 70 mg (4 mol %) | — |
|  | Au/La$_2$O$_3$ (Example 1-13) | — | — | — | — | — | 0.13 g (4 mol %) |
| Solvent | acetic acid | 0.4 mL | 0.7 mL | 0.5 mL | 0.5 mL | 0.4 mL | 0.5 mL |
| Reaction conditions | atmosphere | oxygen gas | oxygen gas | oxygen gas | oxygen gas | air | oxygen gas |
|  | pressure (MPa) | 1.5 | 1.5 | 1.5 | 1.5 | normal pressure | 1.5 |
|  | temperature (° C.) | 150 | 150 | 150 | 150 | 125 | 150 |
| Result | yield (%) | 13 | 1 | 21 | 27 | 12 | 3 |
|  | s/a ratio | 3 | 100 | 7 | 14 | 10 | 3 |

TABLE 5

|  |  | Example 2-19 | Example 2-20 | Example 2-21 | Example 2-22 | Example 2-23 | Example 2-24 |
| --- | --- | --- | --- | --- | --- | --- | --- |
| Substrate | dimethyl o-phthalate | 0.20 g | 0.20 g | 0.20 g | 0.20 g | 0.20 g | 0.20 g |
| Solid catalyst | Au/Al$_2$O$_3$ (Example 1-14) | 0.10 g (4 mol %) | — | — | — | — | — |
|  | Au/ZrO$_2$ (Example 1-15) | — | 0.10 g (4 mol %) | — | — | — | — |
|  | Au/ZrO$_2$ (Example 1-16) | — | — | 0.10 g (4 mol %) | — | — | — |
|  | Au/TiO$_2$ (Example 1-17) | — | — | — | 0.10 g (4 mol %) | — | — |
|  | Au/CeO$_2$ (Example 1-18) | — | — | — | — | 0.10 g (4 mol %) | — |
|  | Au/CeO$_2$ (Example 1-19) | — | — | — | — | — | 0.10 g (4 mol %) |

TABLE 5-continued

|  |  | Example 2-19 | Example 2-20 | Example 2-21 | Example 2-22 | Example 2-23 | Example 2-24 |
| --- | --- | --- | --- | --- | --- | --- | --- |
| Solvent | acetic acid | 0.5 mL | 0.5 mL | 0.5 mL | 0.5 mL | 0.5 mL | 0.5 mL |
| Reaction conditions | atmosphere | oxygen gas | oxygen gas | oxygen gas | oxygen gas | oxygen gas | oxygen gas |
|  | pressure (MPa) | 1.6 | 1.85 | 1.85 | 1.6 | 1.6 | 1.5 |
|  | temperature (° C.) | 150 | 150 | 140 | 150 | 150 | 150 |
| Result | yield (%) | 23 | 45 | 58 | 31 | 28 | 25 |
|  | s/a ratio | 5 | 8 | 15 | 4 | 7 | 7 |

TABLE 6

|  |  | Example 2-25 | Example 2-26 | Example 2-27 | Example 2-28 | Example 2-29 |
| --- | --- | --- | --- | --- | --- | --- |
| Substrate | dimethyl o-phthalate | 0.20 g | 0.20 g | 0.10 g | 0.40 g | 0.41 g |
| Solid catalyst | Au/Mn$_2$O$_3$ (Example 1-20) | 0.63 g in total (6 mol %) | — | — | — | — |
|  | Au/MnO$_2$ (Example 1-22) | — | 71 mg (4 mol %) | — | — | — |
|  | AU/Co$_3$O$_4$ Example 1-27) | — | — | 36 mg (4 mol %) | — | — |
|  | Au/Co$_3$O$_4$ (Example 1-12) | — | — | — | 0.141 g (4 mol %) | — |
|  | Au/Co$_3$O$_4$ (Example 1-1) | — | — | — | — | 0.142 g (4 mol %) |
| Solvent | acetic acid | 0.4 mL | 0.4 mL | 0.2 mL | — | — |
| Reaction conditions | atmosphere | air | air | air | air | air |
|  | pressure (MPa) | normal pressure | normal pressure | normal pressure | normal pressure | normal pressure |
|  | temperature (° C.) | 125 | 125 | 125 | 150 | 200 |
| Result | yield (%) | 58 | 17 | 7 | 9 | 1 |
|  | s/a ratio | 20 | 28 | 15 | 2 | 2 |

TABLE 7

|  |  | Example 2-30 | Example 2-31 | Example 2-32 | Example 2-33 | Example 2-34 |
| --- | --- | --- | --- | --- | --- | --- |
| Substrate | dimethyl o-phthalate | 0.40 g | 0.21 g | 0.21 g | 0.20 g | 0.20 g |
| Soiid catalyst | Au/Co$_3$O$_4$ (Example 1-12) | 0.144 g (4 mol %) | — | — | — | — |
|  | Au/Ce(La)O$_2$ (Example 1-25) | — | 84 mg (0.4 mol %) | — | — | — |
|  | Au/Ce(Zr)O$_2$ (Example 1-26) | — | — | 84 mg (0.4 mol %) | — | — |
|  | Au/TiO$_2$ (Example 1-5) | — | — | — | 85 mg (0.4 mol %) | — |
|  | Au/Co$_3$O$_4$ (Example 1-1) | — | — | — | — | 72 mg (4 mol %) |
| Solvent | acetic acid | — | 0.4 mL | 0.4 mL | — | — |
|  | 1H,1H-tridecafluoro-1-heptanol | — | — | — | 0.2 mL | 0.3 mL |
| Reaction conditions | atmosphere | air | air | air | air | air |
|  | pressure (MPa) | normal pressure | normal pressure | normal pressure | 2.5 | 2.5 |
|  | temperature (° C.) | 200 | 125 | 125 | 150 | 150 |
| Result | yield (%) | 8 | 9 | 1 | 1 | 1 |
|  | s/a ratio | 2 | 15 | 9 | 1 | 1 |

TABLE 8

|  |  | Example 2-35 | Example 2-36 | Example 2-37 | Example 2-38 | Example 2-39 | Example 2-40 |
| --- | --- | --- | --- | --- | --- | --- | --- |
| Substrate | o-xylene | 0.11 g | 0.11 g | — | — | — | — |
|  | methyl benzoate | — | — | 0.14 g | — | — | — |
|  | toluene | — | — | — | 0.09 g | — | — |
|  | benzoic acid | — | — | — | — | 0.12 g | — |
|  | xylene (mixture of o-, m- and p-form) | — | — | — | — | — | 0.52 g |

TABLE 8-continued

|  |  | Example 2-35 | Example 2-36 | Example 2-37 | Example 2-38 | Example 2-39 | Example 2-40 |
|---|---|---|---|---|---|---|---|
| Solid catalyst | Au/Co$_3$O$_4$ (Example 1-1) | 72 mg (4 mol %) | 72 mg (4 mol %) | 72 mg (4 mol %) | 72 mg (4 mol %) | 72 mg (4 mol %) | — |
|  | Au/MnO$_2$ (Example 1-8) | — | — | — | — | — | 0.15 g (0.8 mol %) |
| Solvent | acetic acid | 0.4 mL | 0.4 mL | 0.4 mL | 0.4 mL | 0.4 mL | — |
| Reaction conditions | atmosphere | nitrogen gas | nitrogen gas | nitrogen gas | nitrogen gas | nitrogen gas | oxygen gas |
|  | pressure (MPa) | 0.5 | normal pressure | normal pressure | 0.5 | normal pressure | 0.5 |
|  | temperature (° C.) | 125 | 125 | 125 | 125 | 125 | 100 |
| Result | yield (%) | 3.2 | 7.5 | 3.3 | — | — | — |

TABLE 9

|  |  | Example 2-41 | Example 2-42 | Example 2-43 | Example 2-44 | Example 2-45 | Example 2-46 |
|---|---|---|---|---|---|---|---|
| Substrate | o-xylene | 0.11 g | — | — | — | — | — |
|  | trifluoromethylbenzene | — | 0.15 g | — | — | — | — |
|  | p-dimethoxybenzene | — | — | 0.14 g | — | — | — |
|  | tert-butylbenzene | — | — | — | 0.13 g | — | — |
|  | o-dimethoxybenzene | — | — | — | — | 0.14 g | — |
|  | 2,3,6-trimethylphenol | — | — | — | — | — | 0.14 g |
| Solid catalyst | Au/Co$_3$O$_4$ (Example 1-1) | 74 mg (4 mol %) | 74 mg (4 mol %) | 74 mg (4 mol %) | 75 mg (4 mol %) | 72 mg (4 mol %) | 72 mg (4 mol %) |
| Solvent | acetic acid | 0.5 mL | 0.5 mL | 0.5 mL | 0.5 mL | 0.4 mL | 0.4 mL |
| Reaction conditions | atmosphere | air | oxygen gas | air | oxygen gas | air | air |
|  | pressure (MPa) | normal pressure | 1.6 | normal pressure | 1.6 | normal pressure | normal pressure |
|  | temperature (° C.) | 130 | 150 | 150 | 150 | 125 | 125 |
| Result | yield (%) | 13 | 4 | 21 | 62 in total | 19 | 46 |
|  | s/a ratio | 7 | — | — | — | — | — |

TABLE 10

|  |  | Comparative Example 2-1 | Comparative Example 2-2 | Comparative Example 2-3 | Comparative Example 2-4 | Comparative Example 2-5 |
|---|---|---|---|---|---|---|
| Substrate | dimethyl o-phthalate | 0.21 g | — | — | — | — |
|  | tert-butylbenzene | — | — | 0.13 g | — | — |
|  | p-dimethoxybenzene | — | — | — | 0.14 g | — |
|  | o-xylene | — | — | — | — | 0.11 g |
| Solid catalyst | Au/Co$_3$O$_4$ (Example 1-1) | — | 75 mg | — | — | — |
|  | CO$_3$O$_4$ | — | — | 66 mg | 66 mg | 66 mg |
| Solvent | acetic acid | 0.4 mL | 0.4 mL | 0.5 mL | 0.5 mL | 0.5 mL |
|  | tetrachloroauric acid tetrahydrate | 24 mg (6 mol %) | — | — | — | — |
| Reaction conditions | atmosphere | air | nitrogen gas | oxygen gas | oxygen gas | air |
|  | pressure (MPa) | normal pressure | normal pressure | 1.6 | 0.2 | normal pressure |
|  | temperature (° C.) | 125 | 125 | 150 | 150 | 150 |
| Result | yield (%) | 0 | — | 0 | 0 | 0 |
|  | detection of gold in filtrate | — | no detection | — | — | — |

From the above results, it was demonstrated that multi-substituted biphenyl compounds can be obtained without any complicated steps in a high yield according to the present invention.

INDUSTRIAL APPLICABILITY

The method for producing a multisubstituted biphenyl compound and the solid catalyst according to the present invention can be applied, for example, the production of a monomer having a biphenyl backbone as a raw material for polyimides and the production of a basic backbone of a liquid crystal molecule.

The invention claimed is:

1. A method for producing a multisubstituted biphenyl compound represented by the following formula (2), comprising:
    a step of coupling a substituted benzene compound represented by the following formula (1) in the presence of a solid catalyst with gold immobilized onto a support, wherein the support is a metal oxide,

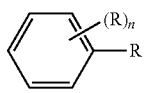

wherein R represents an alkyl group, an alkoxy group, a hydroxy group, or a carboxyl group which may be esterified, and n represents an integer of 0 to 3; when n is any integer of 1 to 3, a plurality of R may be the same or different from each other; and when n is any integer of 1 to 3 and both of two R bonding to adjacent carbon atoms are the carboxyl groups, these carboxyl groups may bond to each other to form an anhydride, and

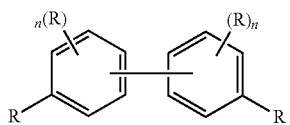

wherein R represents an alkyl group, an alkoxy group, a hydroxy group, or a carboxyl group which may be esterified, and n represents an integer of 0 to 3; a plurality of n and R may be the same or different from each other; and when n is any integer of 1 to 3 and both of two R bonding to adjacent carbon atoms are the carboxyl groups, these carboxyl groups may bond to each other to form an anhydride.

2. The method for producing the multisubstituted biphenyl compound according to claim 1, wherein the substituted benzene compound represented by the formula (1) is a substituted benzene compound represented by the following formula (1)' and the multisubstituted biphenyl compound represented by the formula (2) is a compound represented by the following formula (2)',

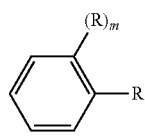

wherein R represents an alkyl group, an alkoxy group, a hydroxy group, or a carboxyl group which may be esterified, and m represents 0 or 1; when m is 1, two R may be the same or different from each other; and when m is 1 and both of two R are the carboxyl groups, these carboxyl groups may bond to each other to form an anhydride, and

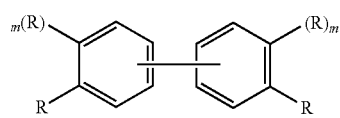

wherein R represents an alkyl group, an alkoxy group, a hydroxy group, or a carboxyl group which may be esterified, and m represents 0 or 1; a plurality of m and R may be the same or different from each other; and when m is 1 and both of two R bonding to adjacent carbon atoms are the carboxyl groups, these carboxyl groups may bond to each other to form an anhydride.

3. The method for producing the multisubstituted biphenyl compound according to claim 1, wherein the R in the formulae (1) and (2) is an alkyl group, a carboxyl group or an alkoxycarbonyl group.

4. The method for producing the multisubstituted biphenyl compound according to claim 2, wherein the R in the formulae (1)' and (2)' is an alkyl group, a carboxyl group or an alkoxycarbonyl group.

5. The method for producing the multisubstituted biphenyl compound according to claim 2, wherein m in the formulae (1)' and (2)' is 1, and a production ratio (s/a ratio) of an s-form represented by the following formula (2s) to an a-form represented by the following formula (2a) in the multisubstituted biphenyl compound represented by the formula (2)' is 2.0 or more,

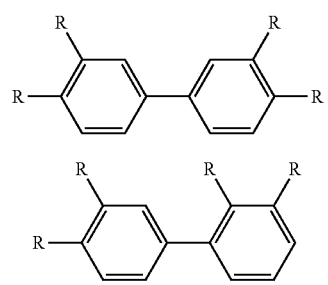

wherein R represents an alkyl group, an alkoxy group, a hydroxy group, or a carboxyl group which may be esterified; a plurality of R may be the same or different from each other; and when both of two R bonding to adjacent carbon atoms are the carboxyl groups, these carboxyl groups may bond to each other to form an anhydride.

6. The method for producing the multisubstituted biphenyl compound according to claim 1, wherein the metal oxide is an oxide of at least one metal selected from the group consisting of cobalt (Co), manganese (Mn), iron (Fe), cerium (Ce), zirconium (Zr), nickel (Ni), titanium (Ti), lanthanum (La), silicon (Si) and aluminum (Al).

7. The method for producing the multisubstituted biphenyl compound according to claim 1, wherein the metal oxide is an oxide of at least one metal selected from the group consisting of manganese (Mn), cobalt (Co) and zirconium (Zr).

8. The method for producing the multisubstituted biphenyl compound according to claim 1, wherein a gold particle having an average particle diameter of 0.5 to 10 nm are immobilized onto the support.

9. The method for producing the multisubstituted biphenyl compound according to claim 1, wherein, in the step of coupling the substituted benzene compound, the substituted benzene compound represented by the formula (1) is coupled further in the presence of a solvent, and the solvent is an organic carboxylic acid.

10. The method for producing the multisubstituted biphenyl compound according to claim 9, wherein the organic carboxylic acid is acetic acid.

11. The method for producing the multisubstituted biphenyl compound according to claim 1, wherein, in the step of coupling the substituted benzene compound, the substituted benzene compound represented by the formula (1) is coupled in the presence of a gas containing oxygen.

\* \* \* \* \*